United States Patent
Kazuta et al.

(10) Patent No.: US 9,018,260 B2
(45) Date of Patent: Apr. 28, 2015

(54) INDANESULFAMIDE DERIVATIVES

(71) Applicant: Eisai R&D Management Co., Ltd., Bunkyo-ku, Tokyo (JP)

(72) Inventors: Yuji Kazuta, Tsukuba (JP); Toru Watanabe, Tsukuba (JP); Keiichi Sorimachi, Tsukuba (JP); Minako Saito, Tsukuba (JP); Yoichi Kita, Tsukuba (JP); Toshiaki Tanaka, Tokyo (JP); Hiroyuki Higashiyama, Tsukuba (JP); Takahisa Hanada, Tsukuba (JP); Tetsuyuki Teramoto, Tsukuba (JP); Takashi Kosasa, Tsukuba (JP); Yukio Ishikawa, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/370,633

(22) PCT Filed: Jun. 17, 2013

(86) PCT No.: PCT/JP2013/066623
§ 371 (c)(1),
(2) Date: Jul. 3, 2014

(87) PCT Pub. No.: WO2013/191144
PCT Pub. Date: Dec. 27, 2013

(65) Prior Publication Data
US 2014/0371319 A1    Dec. 18, 2014

Related U.S. Application Data

(60) Provisional application No. 61/662,626, filed on Jun. 21, 2012, provisional application No. 61/709,737, filed on Oct. 4, 2012, provisional application No. 61/751,331, filed on Jan. 11, 2013.

(51) Int. Cl.
*A61K 31/18* (2006.01)
*C07C 311/00* (2006.01)
*C07C 307/08* (2006.01)
*C07C 309/00* (2006.01)

(52) U.S. Cl.
CPC ............. *C07C 307/08* (2013.01); *C07C 309/00* (2013.01); *A61K 31/18* (2013.01)

(58) Field of Classification Search
CPC ..... C07C 307/08; C07C 309/00; A61K 31/18
USPC .............................................. 514/600; 564/79
See application file for complete search history.

(56) References Cited

U.S. PATENT DOCUMENTS 3,383,414 A    5/1968   Houlihan et al.
3,709,677 A    1/1973   Houlihan

FOREIGN PATENT DOCUMENTS

| JP | 2006-508016 | 3/2006 |
|---|---|---|
| JP | 2011-523656 | 8/2011 |
| WO | 03/063797 | 8/2003 |
| WO | 2009/147167 | 12/2009 |
| WO | 2010/115952 | 10/2010 |

OTHER PUBLICATIONS

Akincioğlu et al., "Novel sulfamides as potential carbonic anhydrase isoenzymes inhibitors", Bioorganic & Medicinal Chemistry 1379-1385 (2013).
Das et al., "An overview on antiepileptic drugs", Drug Discoveries & Therapeutics, 6(4):178-193 (2012).
International Search Report for PCT/JP2013/066623.
Racine, R.J., "Modification of Seizure Activity by Electrical Stimulation: II. Motor Seizure", Electroencephalography and Clinical Neurophysiology, Elsevier Publishing Co., Amsterdam, 32:281-294 (1972).
Asadi-Pooya A and Sperling, "Chapter 1: Diagnosis and Evaluation of Patients with Seizures," in Antiepileptic Drugs; A Clinician's Manual, Oxford university press, 1973, 17 pages.
Browne and Holmes, "Chapter 1: Epilepsy: Definitions and Background," in Handbook of Epilepsy 4th ed., Lippincott Williams & Wilkins, 2008, 26 pages.
Diaz-Arrastia et al., "Evolving treatment strategies for epilepsy," JAMA, Jun. 12, 2002, 287(22):2917-2920.
Elger and Schmidt, "Modern management of epilepsy: a practical approach," Epilepsy & Behavior, 2008, 12:501-539.
Engel and Pedley, "Chapter 1—Introduction: What is Epilepsy?" in Epilepsy: A Comprehensive Textbook 2nd ed., Lippincott Williams & Wilkins, 2008, 10 pages.
LaRoche and Helmers, "The new anti-epileptic drugs," JAMA, Feb. 4, 2004, 291(5):605-614.
Schmidt, "The clinical impact of new anti-epileptic drugs after a decade of use in epilepsy," Epilepsy Res., 2002, 00:1-12.
Treiman, "Management of refractory complex partial seizures: current state of the art," Neuropsychiatric Disease and Treatment, 2010, 6:297-308.
Zaccara et al., "Central nervous system adverse effects of new antiepileptic drugs: A meta-analysis of placebo-controlled studies," Seizure, 2008, 17:405-421.
Eisai R&D Management Co., Ltd., "Experimental data," Jan. 28, 2015, 1page.
Löscher, "Critical review of current animal models of seizures and epilepsy used in the discovery and development of new antiepileptic drugs," Seizure, 20 (2011) 359-368.
Office Action in VN Application No. 1-2014-04194, dated Jan. 29, 2015, 4 pages (with English translation).
International Preliminary Report on Patentability in International Application No. PCT/JP2013/066623, dated Dec. 24, 2014, 4 pages.

*Primary Examiner* — Samantha Shterengarts
(74) *Attorney, Agent, or Firm* — Fish & Richardson P.C.

(57) ABSTRACT

Novel indansulfamide derivatives or a pharmaceutically acceptable salt thereof such as N-[(1S)-2,2,5,7-tetrafluoro-2,3-dihydro-1H-inden-1-yl]sulfamide, N-[(1S)-2,2,4,7-tetrafluoro-2,3-dihydro-1H-inden-1-yl]sulfamide, (+)-N-(2,2,4,6,7-pentafluoro-2,3-dihydro-1H-inden-1-yl)sulfamide, have an action of improving Seizure Severity Index (Score) in mice kindling model. Thus the compounds or the salt thereof are expected as a drug for treating epilepsy.

19 Claims, 3 Drawing Sheets

INDANESULFAMIDE DERIVATIVES

TECHNICAL FIELD

The present invention relates to novel indansulfamide derivatives and an antiepileptic drug comprising thereof.

BACKGROUND ART

Epilepsy is one of the most common disorders of the central nervous system and there are over 50 million sufferers in the world. According to the definition by WHO, epilepsy is "a chronic brain disease of various etiologies characterized by recurrent seizures (epileptic seizures) due to excessive discharges of cerebral neurons, accompanied by a variety of clinical and laboratory manifestations".

As epileptic seizures, for example, partial seizures such as simple partial seizures, complex partial seizures and secondary generalized seizures, absence seizures, myoclonic seizures, tonic seizures, clonic seizures, tonic seizures, tonic-clonic seizures, atonic seizures, West syndrome and Lennox-Gastaut syndrome are known.

The mainstream of treatment of the epilepsy is pharmacotherapy with antiepileptic drugs (AED). The goal of treating epilepsy is to abolish seizures and to prevent side effects during treatment. Treatment by antiepileptic drugs is initiated from a single drug in principle.

The single drug therapy is usually tried by two or three kinds of drugs in turn. If monotherapy is not successful, polytherapy is used. In about 70% of patients with new on-set epilepsy, remission of seizures is expected by monotherapy.

It is known that, however, in the remaining 30 percent of those, pharmacotherapy including polytherapy cannot control their epileptic seizures.

Examples of launched antiepileptic drugs are carbamazepine, ethosuximide, phenobarbital, phenytoin, primidone, sodium valproate, zonisamide, felbamate, gabapentine, lamotrigine, topiramate, tiagabine, levetiracetam, oxcarbazepine, eslicarbazepine, pregabalin, lacosamide, rufinamide, trimethadione, sultiame, acetazolamide, vigabatrin, benzodiazepine derivatives (clonazepam, clobazam, nitrazepam, diazepam), perampanel, retigabine, etc (Non Patent Literature 1).

These known antiepileptic drugs exert an effect by inhibiting neuronal hyperexcitability.

One of the serious problems in therapy by antiepileptic drugs is toxicity due to their inhibitory effect on neurologic function (dizziness, nystagmus, ambiopia, drowsiness, emesis, ataxia, psychological symptom, tiredness and evolition, etc.).

These are side effects that most of these conventional antiepileptic drugs have in a dose-dependent manner, and these are serious problems that lead to limit choice of the therapeutic agents and their dose.

The side effects also worsen the quality of life of epilepsy patients in need of long-term dosing.

Thus, the drugs that are superior in difference between effective dose and neurotoxic doses are in demand.

As 1-indansufamides, the low-molecular compounds in the following Patent Literature 1 and 2, and Non Patent Literature 2 are known.

CITATION LIST

Patent Literature

Patent Literature 1: U.S. Pat. No. 3,383,414
Patent Literature 2: U.S. Pat. No. 3,709,677

Non Patent Literature

Non Patent Literature 1: Shrivastava et al., "An overview on antiepileptic drugs" Drug Discoveries & Therapeutics., Vol. 6, No. 4, pp. 178-193, 2012.
Non Patent Literature 2: Claudiu T. Supuran et al., "Novel sulfamides as potential carbonic anhydrase isoenzymes inhibitors", Bioorg. Med. Chem., Vol. 21, 1379-1385, 2013.

SUMMARY OF INVENTION

Technical Problem

An object of the present invention is to provide a novel compound having an action of improving Seizure Severity Index (Score) in mice kindling model.

Solution to Problem

Mouse corneal kindling model is known as a simple and useful experimental model of epilepsy. (Epilepsy Research Vol. 92, 2010, p 163-169) The present inventors have continued screening using kindled animal model as epilepsy model. And the present inventors have also continued intensive studies on reducing neurotoxic effect.

As a result of the studies, the present inventors have discovered that novel 1-indansulfamide compounds have strong inhibitory effect on epilepsy and achieved the present invention.

Specifically, the present invention relates to:
[1] A compound or pharmaceutically acceptable salt thereof, which is selected from the group:
1) N-[(1S)-2,2,5,7-tetrafluoro-2,3-dihydro-1H-inden-1-yl]sulfamide,
2) N-[(1S)-2,2,4,7-tetrafluoro-2,3-dihydro-1H-inden-1-yl]sulfamide,
3) (+)-N-(2,2,4,6,7-pentafluoro-2,3-dihydro-1H-inden-1-yl)sulfamide,
4) N-[(1S*)-5-cyano-2,2-difluoro-7-methyl-2,3-dihydro-1H-inden-1-yl]sulfamide,
5) (−)-N-(2,2,6,7-tetrafluoro-2,3-dihydro-1H-inden-1-yl)sulfamide,
6) (−)-N-(7-chloro-2,2,5-trifluoro-2,3-dihydro-1H-inden-1-yl)sulfamide,
7) (−)-N-(7-chloro-2,2,4-trifluoro-2,3-dihydro-1H-inden-1-yl)sulfamide,
8) (−)-N-(7-chloro-2,2-difluoro-2,3-dihydro-1H-inden-1-yl)sulfamide,
9) (−)-N-(7-chloro-2,2,6-trifluoro-2,3-dihydro-1H-inden-1-yl)sulfamide,
10) (+)-N-(5-chloro-2,2,7-trifluoro-2,3-dihydro-1H-inden-1-yl)sulfamide,
11) N-[(1S)-2,2-difluoro-7-methyl-2,3-dihydro-1H-inden-1-yl]sulfamide,
12) N-[(1S)-2,2,5-trifluoro-7-methyl-2,3-dihydro-1H-inden-1-yl]sulfamide,
13) N-[(1S*)-2,2,4-trifluoro-7-methyl-2,3-dihydro-1H-inden-1-yl]sulfamide,
14) N-[(1S*)-7-(difluoromethyl)-2,2-difluoro-2,3-dihydro-1H-inden-1-yl]sulfamide,
15) N-[(1R*,2R*)-2,4,7-trifluoro-2,3-dihydro-1H-inden-1-yl]sulfamide,
16) (−)-N-[(1R*,2R*)-7-chloro-2,4-difluoro-2,3-dihydro-1H-inden-1-yl]sulfamide,
17) (+)-N-[(1R*,2R*)-7-chloro-2,4-difluoro-2,3-dihydro-1H-inden-1-yl]sulfamide, 18) (−)-N-[(1R*,2R*)-7-chloro-2,5-difluoro-2,3-dihydro-1H-inden-1-yl]sulfamide,
19) (+)-N-[(1R*,2R*)-4-chloro-7-fluoro-2-methoxy-2,3-dihydro-1H-inden-1-yl]sulfamide,
20) (+)-N-(7-chloro-4-fluoro-2,3-dihydro-1H-inden-1-yl)sulfamide,
21) (±)-N-(5-fluoro-7-methyl-2,3-dihydro-1H-inden-1-yl)sulfamide,
22) (−)-N-(4-fluoro-7-methyl-2,3-dihydro-1H-inden-1-yl)sulfamide,
23) (+)-N-(4-fluoro-7-methyl-2,3-dihydro-1H-inden-1-yl)sulfamide,
24) (+)-N-(7-methyl-2,3-dihydro-1H-inden-1-yl)sulfamide,
25) (±)-N-(5-chloro-7-methyl-2,3-dihydro-1H-inden-1-yl)sulfamide,
26) (−)-N-(4-chloro-7-fluoro-2,3-dihydro-1H-inden-1-yl)sulfamide,
27) (+)-N-(7-chloro-5-cyano-2,3-dihydro-1H-inden-1-yl)sulfamide,
28) (−)-N-(7-chloro-5-cyano-2,3-dihydro-1H-inden-1-yl)sulfamide,
29) (−)-N-(5-chloro-7-fluoro-2,3-dihydro-1H-inden-1-yl)sulfamide,
30) N-[(1S)-4,7-difluoro-2,3-dihydro-1H-inden-1-yl]sulfamide,
31) (+)-N-(7-chloro-2,3-dihydro-1H-inden-1-yl)sulfamide,
32) (+)-N-(5-cyano-7-methyl-2,3-dihydro-1H-inden-1-yl)sulfamide,
33) (−)-N-(5-cyano-7-methyl-2,3-dihydro-1H-inden-1-yl)sulfamide,
34) N-[(1S)-7-chloro-5-fluoro-2,3-dihydro-1H-inden-1-yl]sulfamide and
35) (−)-N-(4,6,7-trifluoro-2,3-dihydro-1H-inden-1-yl)sulfamide;

[2] A compound or pharmaceutically acceptable salt thereof, which is selected from the group:
1) N-[(1S)-2,2,5,7-tetrafluoro-2,3-dihydro-1H-inden-1-yl]sulfamide,
2) N-[(1S)-2,2,4,7-tetrafluoro-2,3-dihydro-1H-inden-1-yl]sulfamide,
3) (−)-N-(2,2,6,7-tetrafluoro-2,3-dihydro-1H-inden-1-yl)sulfamide,
4) (−)-N-(7-chloro-2,2,5-trifluoro-2,3-dihydro-1H-inden-1-yl)sulfamide,
5) (−)-N-(7-chloro-2,2-difluoro-2,3-dihydro-1H-inden-1-yl)sulfamide,
6) N-[(1S)-2,2-difluoro-7-methyl-2,3-dihydro-1H-inden-1-yl]sulfamide,
7) N-[(1S)-2,2,5-trifluoro-7-methyl-2,3-dihydro-1H-inden-1-yl]sulfamide,
8) N-[(1S)-4,7-difluoro-2,3-dihydro-1H-inden-1-yl]sulfamide,
9) N-[(1S)-7-chloro-5-fluoro-2,3-dihydro-1H-inden-1-yl]sulfamide and
10) (−)-N-(4,6,7-trifluoro-2,3-dihydro-1H-inden-1-yl)sulfamide;

[3] N-[(1S)-2,2,5-trifluoro-7-methyl-2,3-dihydro-1H-inden-1-yl]sulfamide or a pharmaceutically acceptable salt thereof;
[4] (−)-N-(2,2,6,7-tetrafluoro-2,3-dihydro-1H-inden-1-yl)sulfamide or a pharmaceutically acceptable salt thereof;
[5] (−)-N-(7-chloro-2,2,5-trifluoro-2,3-dihydro-1H-inden-1-yl)sulfamide or a pharmaceutically acceptable salt thereof;
[6] N-[(1S)-2,2,5,7-tetrafluoro-2,3-dihydro-1H-inden-1-yl]sulfamide or a pharmaceutically acceptable salt thereof;
[7] N-[(1S)-2,2-difluoro-7-methyl-2,3-dihydro-1H-inden-1-yl]sulfamide or a pharmaceutically acceptable salt thereof;
[8] N-[(1S)-4,7-difluoro-2,3-dihydro-1H-inden-1-yl]sulfamide or a pharmaceutically acceptable salt thereof; and
[9] A pharmaceutical composition for the treatment of epilepsy comprising the compound or pharmaceutically acceptable salt thereof according to any one of [1] to [8] above.

Advantageous Effects of Invention

The compounds or a pharmaceutically acceptable salt thereof according to the present invention have an effect of inhibiting seizure ($ED_{50}$) in mouse kindling model. Thus the compounds of the present invention can be used as a therapeutic agent for treating epilepsy.

DESCRIPTION OF EMBODIMENTS

Figure 1:
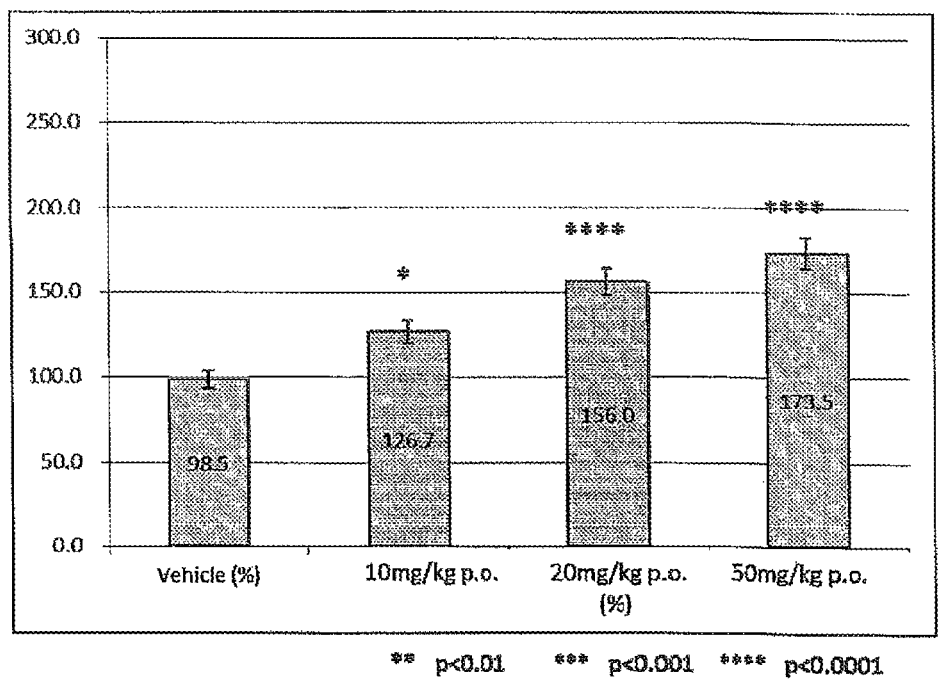
FIG. 1 is a graph showing a result of Test Example 2 by administrating Compound of Example 1.

The present invention is described in detail in the following.

Although crystal polymorphs of the compound may be present, the compound is not limited any one of the polymorphs and may be present as a single crystal form or a mixture of single crystal forms. The compound also includes amorphous.

Furthermore, the compound according to the present invention may form a pharmaceutically acceptable salt, or various solvates.

Hereinafter, the meanings of terms, symbols and the like described in the present specification is explained.

The "pharmaceutically acceptable salt" in the present specification is not particularly limited insofar as it forms a salt with the compound and is pharmaceutically acceptable.

A solvate means a state where a solvent used in reaction or crystallization is incorporated in crystal, without forming a covalent bond with the molecule or ion of the compound. Examples of a solvate are hydrate, ethanolate and the like.

Starting material compounds, intermediates and various reagents in the production of the Compound may form salts or solvates, all vary depending on the starting material, the solvent used or the like, and are not particularly limited insofar as they do not inhibit the reaction. Also, the solvent used varies depending on the starting material, the reagent or the like, and is not particularly limited insofar as it does not inhibit the reaction and dissolves the starting material to a certain extent, obviously. When the compounds are obtained as free forms, they can be converted to acceptable salts or solvates by conventional methods.

Various isomers of the compounds or the intermediates of the present invention (such as geometric isomers, optical isomers, rotamers, stereoisomers, tautomers and the like) can be purified and isolated using common separation methods, for example, recrystallization, diastereomeric salt formation, enzymatic resolution and various chromatography methods (such as thin layer chromatography, column chromatography and gas chromatography).

The compounds or pharmaceutically acceptable salts thereof can be formulated by conventional methods, and examples of dosage forms include oral formulations (such as tablets, granules, powders, capsules and syrups), injections (for intravenous administration, intramuscular administration, subcutaneous administration and intraperitoneal administration) and external preparations (such as transdermal absorption formulations (such as ointments and patches), nasal preparations and suppositories).

The oral solid formulations such as tablets, capsules, granules and powders may contain usually 0.001 to 99.5 wt %, preferably 0.01 to 90 wt % or the like, of the compounds or pharmaceutically acceptable salts thereof.

When oral solid formulations are manufactured, tablets, granules, powders and capsules can be prepared by adding diluents, binders, disintegrants, lubricants, colorants or the like to the compounds or pharmaceutically acceptable salts thereof as necessary and treating by conventional methods. These formulations may also be film coated as necessary.

Examples of diluents include lactose, corn starch and microcrystalline cellulose, examples of binders include hydroxypropylcellulose and hydroxypropylmethylcellulose, and examples of disintegrants include carboxymethylcellulose calcium and croscarmellose sodium.

Examples of lubricants include magnesium stearate and calcium stearate, and examples of colorants include titanium oxide.

Examples of film coating agents include hydroxypropylcellulose, hydroxypropylmethylcellulose and methylcellulose.

Any excipients described above are not limited to these examples, obviously.

When injections (for intravenous administration, intramuscular administration, subcutaneous administration and intraperitoneal administration) are manufactured, they can be manufactured by adding pH adjusters, buffers, suspending agents, solubilizing agents, antioxidants, preservatives (antiseptics), tonicity adjusting agents or the like to the compounds or pharmaceutically acceptable salts thereof as necessary and treating by conventional methods. Lyophilized formulations to be dissolved before use may also be prepared by lyophilization. These injections can be administered intravenously, subcutaneously and intramuscularly, for example.

Examples of pH adjusters and buffers include organic acids or inorganic acids and/or salts thereof, examples of suspending agents include methylcellulose, polysorbate 80 and carboxymethylcellulose sodium, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of tonicity adjusting agents include glucose, sodium chloride and mannitol; however, the excipients are not limited to these examples, obviously.

These injections may contain usually 0.00001 to 99.5 wt %, preferably 0.0001 to 90 wt % of the compounds or pharmaceutically acceptable salts thereof.

When external preparations are manufactured, transdermal absorption formulations (such as ointments and patches), nasal drops, suppositories and the like can be manufactured by adding base materials and, as necessary, the emulsifiers, preservatives, pH adjusters, colorants and the like described above to the compounds or pharmaceutically acceptable salts thereof, and treating by conventional methods.

Conventionally used various raw materials for pharmaceuticals, quasi drugs, cosmetics and the like can be used as base materials, and examples include raw materials such as animal and vegetable oils, mineral oils, ester oils, waxes, higher alcohols and purified water.

These external preparations may contain usually 0.00001 to 99.5 wt %, preferably 0.0001 to 90 wt % of the compounds or pharmaceutically acceptable salts thereof.

A dosage of the medicine according to the present invention typically varies depending on the symptom, age, sex, weight or the like, but is acceptable if it is a dosage sufficient to produce a desired effect. For example, for an adult, a dosage of about 0.1 to 5000 mg (preferably 0.5 to 1000 mg, more preferably 1 to 600 mg) per day is used in one dose during one or more days or in 2 to 6 divided doses for one day.

The present invention also includes the isotopically labeled compounds, and such compounds are the same as the compounds, except that one or more atoms are replaced with an atom(s) having an atomic mass or mass number different from an atomic mass or mass number commonly found in nature. Isotopes that can be incorporated into the compounds are isotopes of hydrogen, carbon, nitrogen, oxygen, phosphorus, fluorine, sulfur and chlorine, for example, and include $^2$H, $^3$H, $^{11}$C, $^{14}$C, $^{13}$N, $^{15}$O, $^{18}$F, $^{32}$P and $^{35}$S.

The compounds or pharmaceutically acceptable derivatives thereof (such as salts) containing the above-described isotopes and/or other isotopes fall within the claims of the present specification. The isotopically labeled compounds of the present invention, for example, compounds into which radioisotopes such as $^3$H and/or $^{14}$C are incorporated, are useful for tissue distribution assays for medicines and/or substrates. $^3$H and $^{14}$C are considered to be useful because of their ease in preparation and detection. Isotopes $^{11}$C and $^{18}$F are considered to be useful for PET (positron emission tomography), and all these isotopes are useful for brain imaging. Replacement with heavier isotopes such as $^2$H produces certain therapeutic advantages such as an increase in the in vivo half-life due to higher metabolic stability, or a reduction in the required dose, and is therefore considered to be useful under certain circumstances. The isotopically labeled compounds can be uniformly prepared by performing the procedures disclosed in the examples using readily available isotopically labeled reagents in place of non-isotopically labeled reagents.

The compounds can be used as chemical probes to trap target proteins in bioactive low molecular weight compounds. Specifically, the compound can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn., Vol. 51, No. 5, 2003, pp. 492-498 or WO 2007/139149 or the like.

Examples of labeling groups, linkers or the like used for chemical probes include groups shown in the group consisting of (1) to (5) below:

(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group in which an α-carbon atom is replaced with a halogen atom, a carbamoyl group, an ester group, an alkylthio group, Michael receptors such as α,β-unsaturated ketones and esters, and an oxirane group), (2) cleavable linkers such as —S—S—, —O—Si—O—, monosaccharides (such as a glucose group and a galactose group) or disaccharides (such as lactose), and oligopeptide linkers cleavable by enzymatic reaction, (3) fishing tag groups such as biotin and a 3-(4,4-difluoro-5,7-dimethyl-4H-3a,4a-diaza-4-bora-s-indacen-3-yl)propionyl group, (4) detectable markers such as radiolabeling groups such as $^{125}$I, 32P, $^3$H and $^{14}$C; fluorescence labeling groups such as fluorescein, rhodamine, dansyl, umbelliferone, 7-nitrofurazanyl and a 3-(4,4-difluoro-5,7-dimethyl-4H-3a,4a-diaza-4-bora-s-indacen-3-yl)propionyl group; chemiluminescent groups such as luciferin and luminol; and heavy metal ions such as lanthanoid metal ions and radium ions; or (5) groups bound to solid phase carriers such as glass beads, glass beds, microtiter plates, agarose beads, agarose beds, polystyrene beads, polystyrene beds, nylon beads and nylon beds.

Probes prepared by introducing labeling groups or the like selected from the group consisting of (1) to (5) above into the compounds according to the method described in the above documents or the like can be used as chemical probes for identification of labeled proteins useful for searching for novel drug targets, for example.

EXAMPLES

The Compounds can be produced by the methods described in examples below, for example, and the effects of the compounds can be confirmed by the methods described in test examples below. However, these methods are illustrative and may be changed without departing from the scope of the present invention and the present invention is not limited to the following specific examples in any case.

Compounds, to which publication names or the like are attached, were produced in accordance with the publications or the like.

All of the abbreviations used in this description are conventional ones known to those in the art. The following abbreviations are used in the following examples.
AcOEt: ethyl acetate
BAST: bis(2-methoxyethyl)aminosulfur trifluoride
Bn: benzyl
Boc: tert-butoxycarbonyl
DCM: dichloromethane
DMF: N,N-dimethylformamide
DMSO: dimethylsulfoxide
$^1$H-NMR: proton Nuclear Magnetic Resonance spectrometry
HPLC: High Performance Liquid Chromatography
I.D.: Internal Diameter
LC-MS: liquid chromatography-mass spectrometry
m-: meta-
n-: normal-
NBS: N-bromosuccinimide
o-: ortho-
p-: para-
PPTS: pyridinium p-toluenesulfonate
Selectfluor™:
N-fluoro-N'-chloromethyl-triethylenediamine-bis(tetrafluoroborate)
t-: tertiary-
TBS: tert-butyldimethylsilyl
TEA: triethylamine
THF: tetrahydrofuran
THP: tetrahydropyran
Z(Cbz): benzyloxycarbonyl The "room temperature" in the following examples and preparation examples typically refers to about 10° C. to about 35° C. "%" indicates wt % unless otherwise specified. The ratio of the solvents in silica gel chromatography shows the volume ratio of the solvents to be admixed.

Chemical shifts in proton nuclear magnetic resonance spectra are recorded in δ units (ppm) relative to tetramethylsilane and coupling constants are recorded in Hertz (Hz). Patterns are designated as s: singlet, d: doublet, t; triplet, q: quartet, m: multiplet, brs; broad singlet.

Optical resolution of the compounds performed by GILSON HPLC system (Pump; Master Pump Model 305, Slave Pump Model 306, Pumphead 50SC, Dynamic mixer Model 811D/A, Manometric Module Model 806, UV detector; UV/VIS detector Model 155, Injector, Fraction collector; Model 215, Column; Selected from DAICEL CHIRALPAK® AD-H, IA, IB, IC, ID, IE, IF, DAICEL CHIRALCEL®, OD-H, OJ-H, 20 mm I.D.×250 mm).

After detection of fractions by the UV detector, optical rotation (+/−) was measured using the optical rotation detector (OR-2090, JASCO, mercury-xenon (Hg—Xe) lamp, 150 W).

With respect to chromatography, if there is described a silica gel column chromatography, YAMAZEN parallel prep (column: YAMAZEN Hi-Flash™ Column (Silicagel), size; S (16×60 mm), M (20×75 mm), L (26×100 mm), 2 L (26×150 mm) or 3 L (46×130 mm)), spherical silica gel for chromatography PSQ 60B™ of FUJI SILYSIA CHEMICAL CO., LTD., silica gel for chromatography BW-300™ of Fuji Silysia Chemical Co., Ltd., Wakogel® C-200 (Wako Pure Chemical Industries, Ltd.), or silicagel 60 (70-230 mesh) of Merck Ltd. Japan was used.

Also, if there is a description with NH silica gel column chromatography, YAMAZEN parallel prep (column: YAMAZEN Hi-Flash™ Column (Amino), size; S (16×60 mm), M (20×75 mm), L (26×100 mm), 2 L (26×150 mm) or 3 L (46×130 mm)) or NH SILICA GEL (200-350 mesh) of FUJI SILYSIA CHEMICAL CO., LTD. was used.

In the nomenclature of compounds in the present specification, (±) and (RS) represent racemic mixture, and (+)-, (−)-, (R) and (S) represent (+), (−), (R) and (S) configurations of the enantiomers, respectively. And "*" in the steric configuration shows the relative configuration, and unless specifically indicated, it means a certain enantiomer.

Furthermore, the indication "(1R*,2R*)-" shall represent the relationships between the chiral centers in terms of relative configuration, i.e., a certain enantiomer having (1R,2R) or (1S,2S) configuration.

Example 1

Synthesis of N-[(1S)-2,2,5,7-tetrafluoro-2,3-dihydro-1H-inden-1-yl]sulfamide

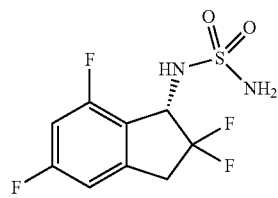

(1)

Synthesis of
2,5,7-trifluoro-2,3-dihydro-1H-inden-1-one

Selectfluor™ (1.16 g, 3.27 mmol) was added to a solution of 5,7-difluoro-1-indanone (CAS No. 84315-25-3, 500 mg, 2.97 mmol) in MeOH (20 mL) at room temperature. The mixture was refluxed for 2 hours and cooled to room temperature. Then the solvent was distilled off under reduced pressure. The residue was treated with DCM and the insoluble matter was filtered off. Then the solvent was distilled off under reduced pressure. The residue was dissolved in MeCN (10 mL) and 5 N HCl (5 mL). The solution was stirred at room temperature for 1 hour, and then concentrated in vacuo. The residue was partitioned between AcOEt and $H_2O$. The organic layer was washed with brine, dried over $MgSO_4$, and concentrated in vacuo to afford the title compound (547 mg, 2.94 mmol). $^1$H NMR (400 MHz, CDCl$_3$)

δ ppm 3.11-3.36 (m, 1H) 3.49-3.77 (m, 1H) 5.10-5.40 (m, 1H) 6.82 (td, J=9.0, 1.9 Hz, 1H) 6.90-7.04 (m, 1H).

(2) Synthesis of
2,2,5,7-tetrafluoro-2,3-dihydro-1H-inden-1-one

t-Butyldimethylsilyl trifluoromethanesulfonate (1.00 mL, 4.35 mmol) was added to a solution of the product obtained in Example 1-(1) (540 mg, 2.90 mmol) and TEA (1.21 mL, 8.70 mmol) in DCM (20 mL) at 0° C. The mixture was stirred at room temperature for 5 hours. Then to the reaction mixture were added diethyl ether and saturated aqueous $Na_2CO_3$ and the layers were separated. The organic layer was successively washed with 1N HCl, saturated aqueous $Na_2CO_3$, and brine, and dried over $Na_2SO_4$. The solvent was evaporated in vacuo and the residue was dried under reduced pressure.

The residue was dissolved in MeCN (20 mL), and Selectfluor™ (1.13 g, 3.19 mmol) was added at room temperature. After stirring the mixture at the same temperature for 11 hours, the solvent was distilled off under reduced pressure. The residue was dissolved in DCM and insoluble matter was filtered off. The filtrate was concentrated in vacuo. The residue was purified by flash column chromatography (Yamazen HI-FLASH™ column Silicagel L size, 20 mL/min, gradient 10% to 50% AcOEt in n-heptane) to afford the title compound as white solids (532 mg, 2.61 mmol).

$^1$H NMR (400 MHz, CDCl$_3$)

δ ppm 3.57 (t, J=12.4 Hz, 2H) 6.74-6.94 (m, 1H) 6.95-7.08 (m, 1H).

(3) Synthesis of
2,2,5,7-tetrafluoro-2,3-dihydro-1H-inden-1-amine

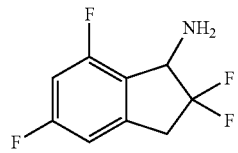

Ammonium acetate (4.27 g, 55.4 mmol) was added to a solution of the product obtained in Example 1-(2) (377 mg, 1.85 mmol) in isopropanol (16 mL) at room temperature and the mixture was refluxed for 30 min. Sodium cyanoborohydride (348 mg, 5.54 mmol) was added to the reaction mixture and stirred under reflux for 7 hours. After cooling to room temperature, AcOEt and 2N NaOH were added to the reaction mixture, and the layers were separated. The organic layer was concentrated in vacuo. Water was added to the residue, and partitioned between AcOEt and 1N HCl. The aqueous layer was basified with 2N NaOH and extracted with AcOEt. The organic layer was dried over $Na_2SO_4$, evaporated and dried to afford the title compound as a yellow oil (210 mg, 1.02 mmol).

ESI-MS; m/z 206 [M+H]$^+$.

$^1$H NMR (400 MHz, CDCl$_3$)

δ (ppm): 3.26-3.55 (m, 2H) 4.59 (dd, J=13.3, 5.3 Hz, 1H) 6.61-6.86 (m, 2H).

(4) Synthesis of benzyl N-(2,2,5,7-tetrafluoro-2,3-dihydro-1H-inden-1-yl)sulfamoylcarbamate

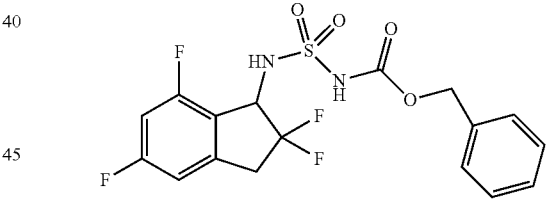

To a DCM solution (10 mL) of the product obtained in Example 1-(3) (200 mg, 0.975 mmol), [(Benzyloxy)carbonyl; {[4-(dimethyliminio)pyridin-1(4H)-yl]sulfonyl}amide (CAS No. 1037211-09-8, 654 mg, 1.95 mmol, prepared according to the method described in WO2008083248) and TEA (0.545 mL, 3.90 mmol) were added at room temperature. The resulting solution was stirred for 24 hours under reflux. After cooling to room temperature, AcOEt and 1N HCl was added to the reaction mixture. The layers were separated, and the organic layer was dried over $MgSO_4$ and evaporated in vacuo. The residue was purified by column chromatography (Silicagel, 30% AcOEt in n-heptane) to afford the title compound as white solids (316 mg, 0.755 mmol).

ESI-MS; m/z 441 [M+Na]$^+$.

$^1$H NMR (400 MHz, CDCl$_3$)

δ (ppm): 3.25-3.54 (m, 2H) 5.14-5.38 (m, 3H) 5.72 (br. s., 1H) 6.72 (t, J=9.4 Hz, 1H) 6.79 (d, J=7.8 Hz, 1H) 7.30-7.46 (m, 5H).

(5) Synthesis of N-[(1S)-2,2,5,7-tetrafluoro-2,3-dihydro-1H-inden-1-yl]sulfamide

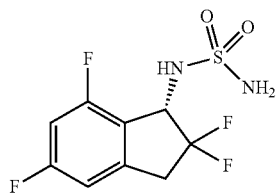 [SMILES: NS(=O)(=O)N[C@H]1c2c(F)cc(F)cc2CC1(F)F]

Palladium-carbon (10 w/w %, 30 mg, 0.028 mmol) was added to a solution of the product obtained in Example 1-(4) (310 mg, 0.741 mmol) in MeOH (5 mL) and AcOEt (5 mL) at 25° C. The resulting solution was stirred for 30 mins at room temperature under $H_2$ atmosphere. AcOEt was added to the reaction mixture, and filtered through Celite® to remove palladium-carbon. The filtrate was concentrated in vacuo. The residue was purified by flash column chromatography (Yamazen HI-FLASH™ column Silicagel M size, 10 mL/min, gradient 30% to 70% AcOEt in n-heptane) to afford the title compound as a racemate (181 mg, 0.637 mmol).

Optical resolution of the obtained racemate (180 mg, 0.633 mmol) was conducted by HPLC (CHIRALPAK™ IA, 20 mm I.D.×250 mm, 10 mL/min, 15% EtOH in hexane) to afford S-form of the title compound as white solids (76 mg, 0.267 mmol. 98% ee), that was eluted second with retention time of 44 min among the 2 isomers.

ESI-MS; m/z307 [M+Na]$^+$.

$^1$H-NMR (400 MHz, CDCl$_3$)

δ (ppm): 3.32-3.60 (m, 2H), 4.70 (brs, 2H), 4.93 (d, J=9.3 Hz, 1H), 5.30 (q, J=9.3 Hz, 1H), 6.70-6.86 (m, 2H).

Example 2

Synthesis of N-[(1S)-2,2,4,7-tetrafluoro-2,3-dihydro-1H-inden-1-yl]sulfamide

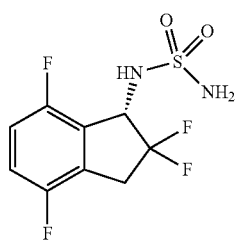 [SMILES: NS(=O)(=O)N[C@H]1c2c(F)ccc(F)c2CC1(F)F]

The title compound (2.13 g, 7.49 mmol) was obtained as a racemate from 4,7-difluoro-1-indanone (CAS No. 130408-16-1, 6.15 g, 36.6 mmol) by a similar method as described in Example 1.

ESI-MS m/z: 307[M+Na]$^+$ $^1$H NMR (400 MHz, CDCl$_3$)

δ (ppm): 3.33-3.63 (m, 2H), 4.73 (br.s., 2H), 5.01 (d, J=8.4 Hz, 1H), 5.35 (q, J=9.8 Hz, 1H), 6.92-7.16 (m, 2H).

Optical resolution of the obtained racemate (180 mg, 0.633 mmol) was conducted by HPLC (CHIRALCEL™ OD-H, 20 mm I.D.×250 mm, 15% EtOH in hexane, 10 mL/min) to afford the title compound (1S)-form as white solid (45 mg, 0.158 mmol. 99% ee), that was eluted second among the 2 optical isomers. As a result of analysis by DAICEL CHIRALCEL™ OD-H (4.6 mm I.D.×150 mm, 15% EtOH in hexane, 1 mL/min), the optical isomer showed retention time of 12 min.

Example 3

Synthesis of (+)-N-(2,2,4,6,7-pentafluoro-2,3-dihydro-1H-inden-1-yl)sulfamide

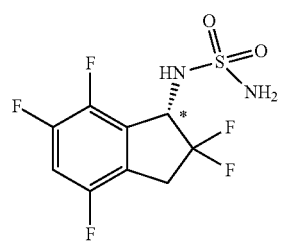 [SMILES: NS(=O)(=O)N[C@H]1c2c(F)c(F)cc(F)c2CC1(F)F]

The title compound (73 mg, 0.242 mmol) was obtained as a racemate from 4,6,7-trifluoro-1-indanone (CAS No. 1260008-80-7, 250 mg, 1.34 mmol) by a similar method as described in Example 1.

Optical resolution of the obtained racemate (70 mg, 0.232 mmol) was conducted by HPLC (CHIRALPAK™ IC, 20 mm I.D.×250 mm, 10% EtOH in hexane, 10 mL/min) to afford the title compound (+)-form (31 mg, 0.103 mmol. >99% ee), that was eluted first with retention time of 40 min among the 2 optical isomers.

ESI-MS; m/z: 325[M+Na]$^+$ $^1$H-NMR (400 MHz, CDCl$_3$)

δ (ppm): 3.34-3.61 (m, 2H), 4.78 (brs, 2H), 5.14 (brs, 1H), 5.29-5.48 (m, 1H), 6.89-7.04 (m, 1H).

Example 4

Synthesis of N-[(1S*)-5-cyano-2,2-difluoro-7-methyl-2,3-dihydro-1H-inden-1-yl]sulfamide

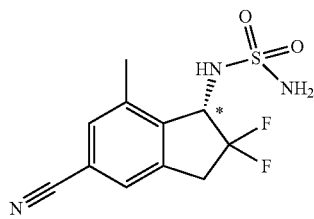 [SMILES: Cc1cc(C#N)cc2c1[C@H](NS(N)(=O)=O)C(F)(F)C2]

(1) Synthesis of 2,2-difluoro-7-methyl-1-oxo-2,3-dihydro-1H-inden-5-carbonitrile

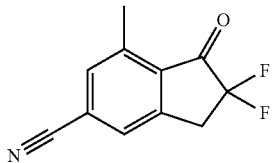

The title compound (600 mg, 2.90 mmol) was obtained from 7-methyl-1-oxoindan-5-carbonitrile (CASNo. 1337833-67-6, 1.00 g, 5.84 mmol) by a similar method as described in Example 1-(1) and 1-(2).

ESI-MS; m/z: 208[M+H]$^+$
$^1$H-NMR (400 MHz, CDCl$_3$)
δ (ppm): 2.71 (s, 3H), 3.57 (t, J=12.8 Hz, 2H), 7.53 (s, 1H), 7.60 (s, 1H).

(2) Synthesis of N-[(1S*)-5-cyano-2,2-difluoro-7-methyl-2,3-dihydro-1H-inden-1-yl]sulfamide

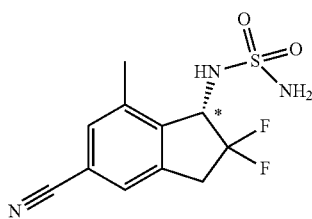 [SMILES: Cc1cc(C#N)cc2c1[C@H](NS(N)(=O)=O)C(F)(F)C2]

The title compound (59.0 mg, 0.205 mmol) was obtained as a racemate from the product of Example 4-(1) (157 mg, 0.759 mmol) by a similar method as described in Example 1-(3) to 1-(5).

Optical resolution of the obtained racemate (59.0 mg, 0.205 mmol) was conducted by HPLC (CHIRALPAK™ IF, 20 mm I.D.×250 mm, 20% EtOH in hexane, 10 mL/min) to afford the title compound (23.4 mg, 0.081 mmol. >99% ee), that was eluted second with retention time of 41 min among the 2 optical isomers.

ESI-MS; m/z: 310[M+Na]$^+$
$^1$H-NMR (400 MHz, DMSO-d$_6$)
δ (ppm): 2.42 (s, 3H), 3.29-3.45 (m, 1H), 3.47-3.63 (m, 1H), 4.86-4.97 (m, 1H), 6.85 (brs, 2H), 7.58-7.70 (m, 3H).

Example 5

Synthesis of (−)-N-(2,2,6,7-tetrafluoro-2,3-dihydro-1H-inden-1-yl)sulfamide

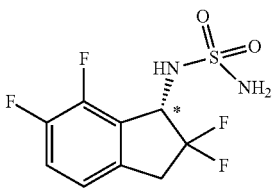 [SMILES: NS(=O)(=O)N[C@H]1c2c(ccc(F)c2F)CC1(F)F]

(1) Synthesis of 2,2,6,7-tetrafluoro-2,3-dihydro-1H-inden-1-amine

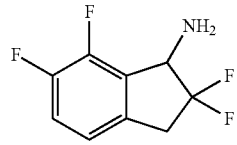 [SMILES: NC1c2c(ccc(F)c2F)CC1(F)F]

4-Bromo-2,6,7-trifluoro-2,3-dihydro-1H-inden-1-one (2.30 g, 8.68 mmol) was obtained from 4-bromo-6,7-difluoro-1-indanone (CAS No. 881189-76-0, 2.45 g, 9.92 mmol) by a similar method as described in Example 1-(1).
4-Bromo-2,2,6,7-tetrafluoro-2,3-dihydro-1H-inden-1-one (1.80 g, 6.38 mmol) was obtained from 4-bromo-2,6,7-trifluoro-2,3-dihydro-1H-inden-1-one (2.30 g, 8.68 mmol) by a similar method as described in Example 1-(2).

Hydroxylamine hydrochloride (0.90 g, 12.8 mmol) was added to a solution of 4-bromo-2,2,6,7-trifluoro-2,3-dihydro-1H-inden-1-one (1.80 g, 6.38 mmol) in EtOH (10 ml) and the reaction mixture was refluxed for 12 hours. After cooling to room temperature, the reaction mixture was concentrated in vacuo.

The residue was successively washed with DCM and water and dried in vacuo. To a solution of the residue in MeOH (20 ml) were added conc. H$_2$SO$_4$ (0.6 ml) and palladium-carbon (90 mg).

The mixture was stirred for 12 hours at room temperature under H$_2$ atmosphere. Palladium-carbon was filtered off and the filtrate was concentrated in vacuo. The residue was purified by silicagel column chromatography to afford the title compound (700 mg, 3.41 mmol).

ESI-MS; m/z: 206[M+H]$^+$

(2) Synthesis of (−)-N-(2,2,6,7-tetrafluoro-2,3-dihydro-1H-inden-1-yl)sulfamide

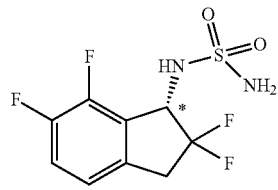 [SMILES: NS(=O)(=O)N[C@H]1c2c(ccc(F)c2F)CC1(F)F]

The title compound (120 mg, 0.423 mmol) was obtained as a racemate from the product obtained in Example 5-(1) (700 mg, 3.41 mmol) by a similar method as described in Example 1-(3) to 1-(5).

Optical resolution of the obtained racemate (110 mg, 0.387 mmol) was conducted by HPLC (CHIRALPAK™ IC, 20 mm I.D.×250 mm, 20% EtOH in hexane, 10 mL/min) to afford the title compound (−)-form (38 mg, 0.134 mmol. >99% ee), that was eluted first with retention time of 20 min among the 2 optical isomers.

ESI-MS; m/z: 307[M+Na]$^+$
$^1$H-NMR (400 MHz, CDCl$_3$)

δ (ppm): 3.29-3.58 (m, 2H), 4.75 (brs, 2H), 5.05 (d, J=9.7 Hz, 1H), 5.38 (q, J=9.7 Hz, 1H), 6.94-7.02 (m, 1H), 7.14-7.23 (m, 1H).

Example 6

Synthesis of (−)-N-(7-chloro-2,2,5-trifluoro-2,3-dihydro-1H-inden-1-yl)sulfamide

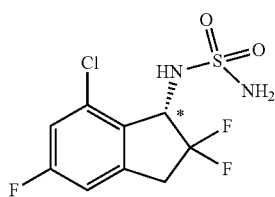
(1)

Synthesis of 7-Chloro-2,5-difluoro-2,3-dihydro-1H-inden-1-one

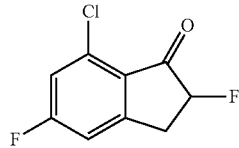

Selectfluor™ (2.49 g, 7.02 mmol) was added to a solution of 7-chloro-5-fluoro-1-indanone (CAS No. 1260008-48-7, 1.08 g, 5.85 mmol) in MeOH (30 mL) at room temperature. The mixture was refluxed for 2 hours. After cooling to room temperature, the resulting mixture was evaporated to remove the solvent under reduced pressure. To the residue was added DCM and the insoluble matter was filtered off. The filtrate was concentrated in vacuo. The residue was dissolved in MeCN (20 mL) and 5 N HCl (10 mL) and the solution was stirred at room temperature for 1 hour. After concentration of the solution in vacuo, the residue was partitioned between AcOEt and H₂O. The organic layer was washed with brine, dried over MgSO₄, and concentrated in vacuo to afford the title compound (1.13 g, 5.58 mmol).

$^1$H-NMR (400 MHz, CDCl₃)

δ ppm 3.13-3.33 (m, 1H) 3.47-3.71 (m, 1H) 5.25 (ddd, J=51.0, 8.0, 4.5 Hz, 1H) 7.07 (dt, J=7.6, 2.0 Hz, 1H) 7.14 (dd, J=8.8, 2.0 Hz, 1H).

(2) Synthesis of 7-Chloro-2,2,5-trifluoro-2,3-dihydro-1H-inden-1-one

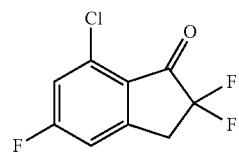 [SMILES: O=C1c2c(Cl)cc(F)cc2CC1(F)F]

t-Butyldimethylsilyl trifluoromethanesulfonate (2.56 mL, 11.2 mmol) was added to a solution of the product obtained in Example 6-(1) (1.13 g, 5.58 mmol) and TEA (3.11 mL, 22.3 mmol) in DCM (30 mL) at 0° C. The mixture was stirred at room temperature for 2 hours. The reaction mixture was diluted with diethyl ether and saturated aqueous Na₂CO₃, and the layers were separated. The organic layer was successively washed with 1N HCl, saturated aqueous Na₂CO₃ and brine, and dried over Na₂SO₄. The solvent was evaporated in vacuo.

The residue was dissolved in MeCN (30 mL), and Selectfluor™ (2.17 g, 6.11 mmol) was added at room temperature. The mixture was stirred at room temperature for 3 hours, and then the resulting mixture was evaporated under reduced pressure. To the residue was added DCM and insoluble matter was filtered off. The filtrate was concentrated in vacuo. The residue was purified by flash column chromatography (Yamazen HI-FLASH™ column Silicagel L size, 20 mL/min, gradient 0% to 30% AcOEt in n-heptane) to afford the title compound (2) (1.11 g, 5.03 mmol).

$^1$H-NMR (400 MHz, CDCl₃)

δ ppm 3.47-3.63 (m, 2H) 7.06-7.13 (m, 1H) 7.17-7.23 (m, 1H).

(3) Synthesis of 7-Chloro-2,2,5-trifluoro-2,3-dihydro-1H-inden-1-amine

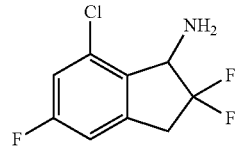

Ammonium acetate (11.5 g, 150 mmol) was added to a solution of the product obtained in Example 6-(2) (1.10 g, 4.98 mmol) in isopropanol (40 mL) at room temperature. The mixture was refluxed for 30 mins. Sodium cyanoborohydride (940 mg, 15.0 mmol) was added to the reaction mixture and the mixture was heated under reflux for 12 hours. After cooling to room temperature, the reaction mixture was diluted with AcOEt, and 2N NaOH was added. The layers were separated and the organic layer was concentrated in vacuo. The residue was partitioned between AcOEt and 1N HCl, and the aqueous layer was basified with 2N NaOH and extracted with AcOEt. The organic layer was dried over Na₂SO₄ and concentrated in vacuo. The residue was purified by flash column chromatography (Yamazen HI-FLASH™ column Silicagel L size, 20 mL/min, gradient 10% to 50% AcOEt in n-heptane) to afford the title compound (3) (699 mg, 3.15 mmol).

$^1$H-NMR (400 MHz, CDCl₃)

δ (ppm): 3.24-3.41 (m, 1H) 3.47-3.65 (m, 1H) 4.50 (d, J=14.6 Hz, 1H) 6.85-6.93 (m, 1H) 7.02 (dd, J=9.0, 2.2 Hz, 1H).

(4) Synthesis of t-Butyl N-(7-chloro-2,2,5-trifluoro-2,3-dihydro-1H-inden-1-yl)sulfamoylcarbamate

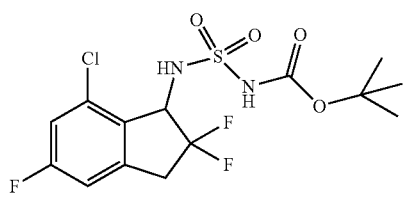 [SMILES: CC(C)(C)OC(=O)NS(=O)(=O)NC1c2c(Cl)cc(F)cc2CC1(F)F]

[(t-butoxy)carbonyl]{[4-(dimethyliminio)pyridin-1(4H)-yl]sulfonyl}amide (CAS No. 872496-91-8, 1.90 g, 6.31 mmol, prepared according to the method described in Organic Letters, 3, 2241 (2001)) and TEA (1.76 mL, 12.6 mmol) was added to a solution of the product obtained in Example 6-(3) (699 mg, 3.15 mmol) in DCM (20 mL) at room temperature. The resulting mixture was heated for 12 hours under reflux. After cooling to room temperature, to the reaction mixture was added AcOEt and 1N HCl and the layers were separated. The organic layer was dried over MgSO$_4$ and evaporated in vacuo. The residue was purified by silicagel column chromatography (Silicagel, 30% AcOEt in n-heptane) to afford the title compound (4) (1.08 g, 2.69 mmol).

$^1$H-NMR (400 MHz, CDCl$_3$)

δ (ppm): 1.49 (s, 9H) 3.28-3.55 (m, 2H) 5.07-5.36 (m, 1H) 5.51-5.70 (m, 1H) 6.89 (d, J=9.2 Hz, 1H) 7.07 (d, J=9.2 Hz, 1H) 7.29 (brs, 1H).

(5) Synthesis of (−)-N-(chloro-2,2,5-trifluoro-2,3-dihydro-1H-inden-1-yl)sulfamide

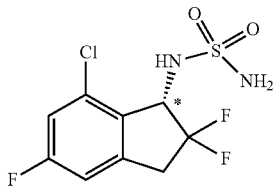 [SMILES: NS(=O)(=O)N[C@H]1c2c(Cl)cc(F)cc2CC1(F)F]

To a solution of the product obtained in Example 6-(4) (1.08 g, 2.69 mmol) in AcOEt (25 mL) was added 4N HCl in AcOEt (26.9 ml, 108 mmol) and the mixture was stirred at room temperature for 5 hours. The solvent was evaporated in vacuo and the residue was purified by silicagel flash column chromatography (Yamazen HI-FLASH™ column L size, 20 mL/min, gradient 30% to 70% AcOEt in n-heptane) to afford the title compound as a racemate (627 mg, 2.09 mmol).

Optical resolution of the obtained racemate (200 mg, 0.665 mmol) was conducted by HPLC (CHIRALPAK™ IB, 20 mm I.D.×250 mm, 10% EtOH in n-hexane, 10 mL/min) to afford the title (−)-form (83 mg, 0.276 mmol, 96% ee), which was eluted second with retention time of 49 min among the 2 optical isomers.

ESI-MS; m/z: 323[M+Na]$^+$ $^1$H-NMR (400 MHz, CDCl$_3$)

δ (ppm): 3.35-3.64 (m, 2H), 4.74 (brs, 2H), 4.86 (d, J=8.6 Hz, 1H), 5.07-5.28 (m, 1H), 6.83-6.95 (m, 1H), 7.09 (dd, J=8.7, 2.3 Hz, 1H).

Example 7

Synthesis of (−)-N-(7-chloro-2,2,4-trifluoro-2,3-dihydro-1H-inden-1-yl)sulfamide

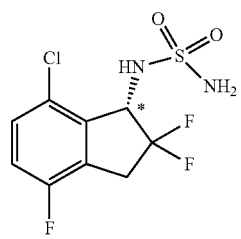 [SMILES: NS(=O)(=O)N[C@H]1c2c(Cl)ccc(F)c2CC1(F)F]

The title compound (183 mg, 0.609 mmol) was obtained as a racemate from 7-chloro-4-fluoro-1-indanone (CAS No. 881190-28-9, 1.70 g, 9.21 mmol) by a similar method as described in Example 6.

Optical resolution of the obtained racemate (110 mg, 0.366 mmol) was conducted by HPLC (CHIRALPAK™ AD-H, 20 mm I.D.×250 mm, 10% EtOH in hexane, 10 mL/min) to afford the title (−)-isomer (46 mg, 0.153 mmol, >99% ee), which was eluted first with retention time of 48 min among the 2 optical isomers.

ESI-MS; m/z: 323[M+Na]$^+$ $^1$H-NMR (400 MHz, CDCl$_3$)

δ (ppm): 3.36-3.63 (m, 2H), 4.74 (brs, 2H), 4.88 (d, J=8.2 Hz, 1H), 5.16-5.34 (m, 1H), 7.06 (t, J=8.4 Hz, 1H), 7.31 (dd, J=8.4, 4.4 Hz, 1H).

Example 8

Synthesis of (−)-N-(7-chloro-2,2-difluoro-2,3-dihydro-1H-inden-1-yl)sulfamide

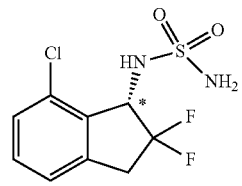

The title compound (1.44 g, 5.09 mmol) was obtained as a racemate from 7-chloro-1-indanone (CAS No. 34911-25-6, 2.48 g, 14.9 mmol) by a similar method as described in Example 6.

Optical resolution of the obtained racemate (430 mg, 1.52 mmol) was conducted by HPLC (CHIRALPAK™ IB, 20 mm I.D.×250 mm, 10% EtOH in hexane, 10 mL/min) to afford the title compound (−)-form (194 mg, 0.686 mmol. >99% ee), that was eluted second with retention time of 43 min among the 2 optical isomers.

ESI-MS; m/z: 305[M+Na]$^+$ $^1$H-NMR (400 MHz, CDCl$_3$)

δ (ppm): 3.35-3.63 (m, 2H), 4.72 (brs, 2H), 4.81 (d, J=8.2 Hz, 1H), 5.24 (ddd, J=12.4, 8.3, 4.2 Hz, 1H), 7.12-7.21 (m, 1H), 7.30-7.37 (m, 2H).

Example 9

Synthesis of (−)-N-(7-chloro-2,2,6-trifluoro-2,3-dihydro-1H-inden-1-yl)sulfamide

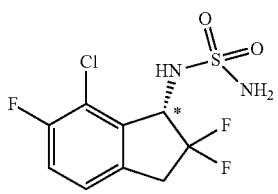 [SMILES: NS(=O)(=O)N[C@H]1c2c(ccc(F)c2Cl)CC1(F)F]

The title compound (243 mg, 0.808 mmol) was obtained as a racemate from 7-chloro-6-fluoro-1-indanone (CAS No. 881190-95-0, 1.00 g, 5.42 mmol) by a similar method as described in Example 6.

Optical resolution of the obtained racemate (200 mg, 0.665 mmol) was conducted by HPLC (CHIRALPAK™ IA, 20 mm I.D.×250 mm, 25% EtOH in hexane, 10 mL/min) to afford the title compound (−)-form (85 mg, 0.283 mmol. >99% ee), that was eluted second with retention time of 24 min among the 2 optical isomers.

ESI-MS; m/z: 323[M+Na]$^+$ $^1$H-NMR (400 MHz, CDCl$_3$)

δ (ppm): 3.33-3.60 (m, 2H), 4.76 (brs, 2H), 4.90 (d, J=7.8 Hz, 1H), 5.16-5.35 (m, 1H), 7.10-7.23 (m, 2H).

Example 10

Synthesis of (+)-N-(5-chloro-2,2,7-trifluoro-2,3-dihydro-1H-inden-1-yl)sulfamide

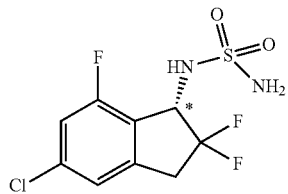 [SMILES: NS(=O)(=O)N[C@H]1c2c(F)cc(Cl)cc2CC1(F)F]

The title compound (149 mg, 0.496 mmol) was obtained as a racemate from 5-chloro-7-fluoro-1-indanone (CAS No. 1273613-81-2, 550 mg, 2.98 mmol) by a similar method as described in Example 6. Optical resolution of the obtained racemate (140 mg, 0.466 mmol) was conducted by HPLC (CHIRALPAK™ IF, 20 mm I.D.×250 mm, 30% EtOH in n-hexane, 10 mL/min) to afford the title compound (+)-form (65.7 mg, 0.283 mmol. >99% ee), that was eluted second with retention time of 23 min among the 2 optical isomers.

ESI-MS; m/z: 323[M+Na]$^+$ $^1$H-NMR (400 MHz, CDCl$_3$)

δ (ppm): 3.30-3.60 (m, 2H), 4.76 (brs, 2H), 5.04 (d, J=9.0 Hz, 1H), 5.21-5.36 (m, 1H), 7.02-7.12 (m, 2H).

Example 11

N-[(1S)-2,2-Difluoro-7-methyl-2,3-dihydro-1H-inden-1-yl]sulfamide

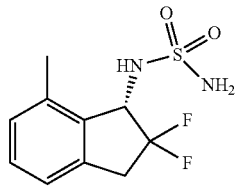 [SMILES: Cc1cccc2c1[C@H](NS(N)(=O)=O)C(F)(F)C2]

(1) Synthesis of 2-Fluoro-7-methyl-2,3-dihydro-1H-inden-1-one

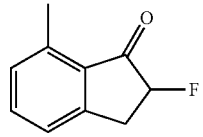

To a solution of 7-methyl-1-indanone (CAS No. 39627-61-7, 513 mg, 3.51 mmol) in MeOH (18 mL) was added Selectfluor™ (1.49 g, 4.21 mmol) at room temperature. The reaction mixture was heated for 2 hours under reflux. After cooling to room temperature, the solvent was evaporated under reduced pressure. The residue was treated with DCM and the insoluble matter was filtered off. The filtrate was concentrated in vacuo. The residue was dissolved in MeCN (10 mL) and 5 N HCl (5 mL). The solution was stirred at room temperature for 30 mins. After concentration of the solution in vacuo, the residue was partitioned between AcOEt and H$_2$O. The aqueous layer was extracted with AcOEt twice. The combined organic layers were washed with brine, dried over MgSO$_4$, filtered and concentrated in vacuo to afford the title compound (555 mg, 3.38 mmol).

$^1$H NMR (400 MHz, CDCl$_3$)

δ ppm 2.64 (s, 3H), 3.18 (ddd, J=23.4, 16.8, 4.3 Hz, 1H), 3.57 (ddd, J=16.8, 7.8, 7.5 Hz, 1H), 5.21 (ddd, J=51.2, 7.8, 4.3 Hz, 1H), 7.17 (d, J=7.4 Hz, 1H), 7.26 (d, J=7.4 Hz, 1H), 7.51 (t, J=7.4 Hz, 1H).

(2) Synthesis of 2,2-Difluoro-7-methyl-2,3-dihydro-1H-inden-1-one

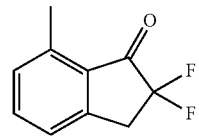

tert-Butyldimethylsilyl trifluoromethanesulfonate (1.55 mL, 6.74 mmol) was added to a solution of the product obtained in Exp. 11-(1) (555 mg, 3.38 mmol) and TEA (1.88 mL, 13.49 mmol) in DCM (30 mL) at 0° C. The mixture was stirred at room temperature for 1.5 hours. The reaction was quenched with sat. NaHCO$_3$, and the layers were separated. The aqueous layer was extracted with DCM. The combined organic layers were washed with brine and dried over MgSO$_4$. The insoluble matter was filtered off and the filtrate was concentrated in vacuo. The residue was dissolved in MeCN (20 mL), and Selectfluor™ (1.32 g, 3.73 mmol) was added at room temperature. After the reaction mixture was stirred for 1 h at room temperature, the solvent was evaporated under reduced pressure. The residue was dissolved in DCM and insoluble matter was filtered off. The filtrate was concentrated in vacuo. The residue was purified by silicagel flash column chromatography (Yamazen HI-FLASH™ column L size, 20 mL/min, gradient 15% to 20% AcOEt in n-heptane) to afford the title compound (563 mg, 3.09 mmol).

¹H-NMR (400 MHz, CDCl₃)

δ ppm 2.66 (s, 3H), 3.51 (t, J=13.1 Hz, 1H), 7.23 (d, J=7.8 Hz, 1H), 7.28 (d, J=7.8 Hz, 1H), 7.57 (t, J=7.8 Hz, 1H).

(3) Synthesis of 2,2-Difluoro-7-methyl-2,3-dihydro-1H-inden-1-ol

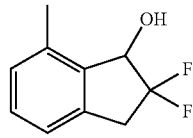

To a solution of the product prepared by the method described in Example 11-(2) (1.09 g, 5.99 mmol) in MeOH (20 mL) was added sodium borohydride (453 mg, 12.0 mmol) at 0° C. After stirring for 45 minutes at the same temperature, water and AcOEt was added to the reaction mixture, and the layers were separated. The aqueous layer separated was extracted with AcOEt twice. The combined organic layer was washed with brine, and dried over MgSO₄. After filtration, the filtrate was concentrated and dried in vacuo to afford the title compound (1.05 g, 5.72 mmol).

¹H-NMR (400 MHz, CDCl₃)

δ ppm 2.23 (br. s, 1H), 2.43 (s, 3H), 3.26-3.39 (m, 1H), 3.44-3.58 (m, 1H), 5.08-5.15 (m, 1H), 7.07 (d, J=7.8 Hz, 1H), 7.10 (d, J=7.8 Hz, 1H), 7.23-7.26 (m, 1H).

(4) Synthesis of 1-Azido-2,2-difluoro-7-methyl-2,3-dihydro-1H-inden

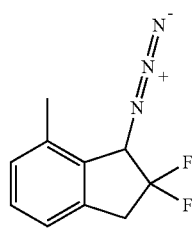

TEA (3.59 ml, 25.8 mmol) and chloromethanesulfonyl chloride (1.02 ml, 11.4 mmol) were added to a solution of the product obtained in Exp. 11-(3) (1.05 g, 5.72 mmol) in DCM (25 mL) at 0° C. After stirring for 2 hours at room temperature, the reaction mixture was diluted with diethyl ether and quenched with sat. NaHCO₃. The aqueous layer was extracted with diethyl ether for 3 times. The combined organic layer was washed with brine and dried over MgSO₄. The extract was filtered and concentrated in vacuo. The residue was dissolved in DMF (50 mL), and sodium azide (753 mg, 11.6 mmol) was added to the solution at room temperature. The reaction mixture was stirred for 2 hours at 70° C. After cooling the mixture to room temperature, water and diethyl ether were added. The layers were separated, and the aqueous layer was extracted with diethyl ether for 3 times. The combined organic layer was washed with water and brine, and dried over MgSO₄. The extract was filtered and concentrated in vacuo. The residue was purified by silicagel flash column chromatography (Yamazen HI-FLASH™ column L size, 20 mL per min, 20% AcOEt in n-heptane) to afford the title compound (641 mg, 3.06 mmol).

¹H-NMR (400 MHz, CDCl₃)

δ ppm 2.41 (s, 3H), 3.30-3.43 (m, 1H), 3.51 (ddd, J=20.3, 16.8, 10.9 Hz, 1H), 4.77 (d, J=13.3 Hz, 1H), 7.09 (d, J=7.4 Hz, 1H), 7.14 (d, J=7.8 Hz, 1H), 7.26-7.31 (m, 1H).

(5) Synthesis of N-(2,2-Difluoro-7-methyl-2,3-dihydro-1H-inden-1-yl)sulfamide

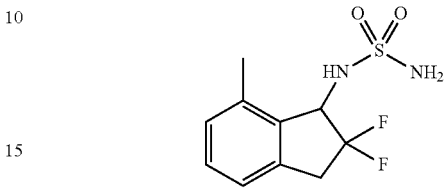

To a solution of the product obtained in Exp. 11-(4) (641 mg, 3.06 mmol) in water (4 ml) and tetrahydrofuran (16 ml) was added triphenyl phosphine (1.21 g, 4.61 mmol) at room temperature. The reaction mixture was stirred for 1 hour at 80° C. After cooling to room temperature, AcOEt (20 mL) and 1N HCl (20 mL) were added. The organic layer separated was extracted with 10 mL of 1N HCl twice. The aqueous layer was combined and basified with 20 mL of 2N NaOH. The layer was extracted with AcOEt for 3 times and the combined organic layer was washed with brine and dried over MgSO₄. The extract was filtered and concentrated in vacuo. To a mixed solution of the residue and TEA (1.1 mL, 7.89 mmol) in DCM (26 mL), sulfamoyl chloride (CAS No. 7778-42-9, 915 mg, 7.92 mmol, prepared according to the method described in US200896903) was added in small portions at room temperature. The reaction mixture was subsequently stirred for 1 hour at room temperature. To the mixture was added 20 mL of 1N HCl, and the aqueous layer was extracted with DCM twice. The combined organic layer was dried over MgSO₄, filtered and concentrated in vacuo. The residue was purified by silicagel flash column chromatography (Yamazen HI-FLASH™ column L size, 20 mL/min, gradient 50% to 65% AcOEt in n-heptane) to afford the title compound (348 mg, 1.33 mmol).

¹H-NMR (400 MHz, CDCl₃)

δ ppm 2.45 (s, 3H), 3.32-3.56 (m, 2H), 4.70-4.80 (m, 3H), 5.17-5.26 (m, 1H), 7.06 (d, J=7.4 Hz, 1H), 7.12 (d, J=7.4 Hz, 1H), 7.23-7.29 (m, 1H).

(6) Synthesis of N-[(1S)-2,2-difluoro-7-methyl-2,3-dihydro-1H-inden-1-yl]sulfamide

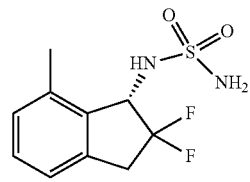 [SMILES: Cc1cccc2c1[C@H](NS(N)(=O)=O)C(F)(F)C2]

Optical resolution of the racemate obtained in Example 11-(5) (348 mg, 1.33 mmol) was conducted by HPLC (CHIRALPAK™ IA, 20 mm I.D.×250 mm, 15% EtOH in n-hexane, 10 mL/min) to afford the title compound (1S)-form (107 mg, 0.409 mmol. >99% ee) as white solids, that was eluted second with retention time of 25 min among the 2 optical isomers.

ESI-MS
m/z: 285[M+Na]⁺

¹H-NMR (400 MHz, CDCl₃)

δ ppm 2.45 (s, 3H), 3.32-3.56 (m, 2H), 4.70-4.80 (m, 3H), 5.17-5.26 (m, 1H), 7.06 (d, J=7.4 Hz, 1H), 7.12 (d, J=7.4 Hz, 1H), 7.23-7.29 (m, 1H).

Example 12

Synthesis of N-[(1S)-2,2,5-Trifluoro-7-methyl-2,3-dihydro-1H-inden-1-yl]sulfamide

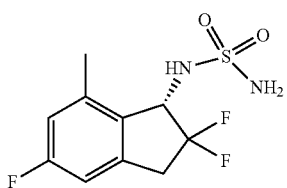 [SMILES: Cc1cc(F)cc2c1[C@H](NS(N)(=O)=O)C(F)(F)C2]

(1) Synthesis of 7-bromo-2,2,5-trifluoro-2,3-dihydro-1H-inden-1-one

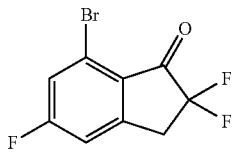

The title compound (5.10 g, 19.2 mmol) was obtained from 7-bromo-5-fluoro-1-indanone (CAS No. 1260016-95-2, 4.55 g, 19.9 mmol) by a similar method as described in Example 5-(1) and 5-(2).

¹H NMR (400 MHz, CDCl₃)

δ ppm 3.53 (t, J=12.5 Hz, 2H), 7.14 (d, J=7.6 Hz, 1H), 7.41 (d, J=8.4 Hz, 1H).

(2) Synthesis of 7-bromo-2,2,5-trifluoro-2,3-dihydro-1H-inden-1-ol

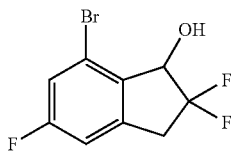

The title compound (4.78 g, 17.9 mmol) was obtained from the product obtained in Example 12-(1) (5.10 g, 19.2 mmol) by a similar method as described in Example 11-(3).

¹H-NMR (400 MHz, CDCl₃)

δ (ppm): 2.50 (s, 1H), 3.38 (td, J=17.0, 2.7 Hz, 1H), 3.50-3.69 (m, 1H), 5.06 (dd, J=12.5, 4.3 Hz, 1H), 6.95 (dd, J=8.0, 1.0 Hz, 1H), 7.22 (dd, J=8.6, 2.3 Hz, 1H).

(3) Synthesis of 2-[(7-bromo-2,2,5-trifluoro-2,3-dihydro-1H-inden-1-yl)oxy]tetrahydro-2H-pyran

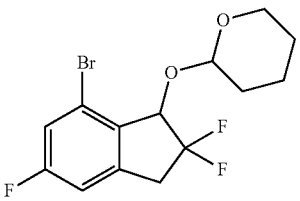 [SMILES: Fc1cc(Br)c2c(c1)CC(F)(F)C2OC1CCCCO1]

To a solution of the product obtained in Example 12-(2) (2.78 g, 10.4 mmol) and 3,4-dihydro-2H-pyran (2.18 mL, 23.9 mmol) in DCM (40 ml) was added PPTS (52 mg, 0.208 mmol) at room temperature. And the reaction mixture was stirred for 86 hours at room temperature. The solvent was evaporated and the residue was purified by flash silicagel column chromatography (Yamazen HI-FLASH™ column M size, 10 mL/min, gradient 10% to 25% AcOEt in n-heptane) to afford the title compound (3.42 g, 9.74 mmol) as about a 1:1 mixture of racemic diastereomers.

¹H-NMR (400 MHz, CDCl₃)

δ (ppm): 1.51-1.84 (m, 6H), 3.26-3.52 (m, 1H), 3.52-3.68 (m, 2H), 4.05-4.19 (m, 1H), 5.00-5.21 (m, 2H), 6.92 (d, J=8.2 Hz, 1H), 7.21 (dt, J=8.2, 2.6 Hz, 1H).

(4) Synthesis of 2-[(2,2,5-trifluoro-7-methyl-2,3-dihydro-1H-inden-1-yl)oxy]tetrahydro-2H-pyran

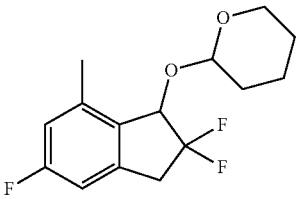 [SMILES: Cc1cc(F)cc2c1C(OC1CCCCO1)C(F)(F)C2]

To a solution of the product obtained in Example 12-(3) (1.70 g, 4.84 mmol) in 1,4-dioxane (10 ml) was added dropwise a 2M n-hexane solution of dimethyl zinc (4.84 ml, 9.68 mmol).

After addition of [1,1'-bis(diphenylphosphino)ferrocene]dichloro palladium(II) (177 mg, 0.242 mmol), the reaction mixture was stirred for 3 hours at 100° C. under nitrogen atmosphere. After cooling to room temperature, water was added and the mixture was extracted with AcOEt. The organic layer was washed with brine and dried over anhydrous Na₂SO₄. The insoluble matter was filtered off and the filtrate was evaporated in vacuo. The residue was purified by flash silicagel column chromatography (Yamazen HI-FLASH™ column Silicagel M size, 10 mL/min, gradient 0% to 25% AcOEt in n-heptane) to afford the title compound as about a 1:1 mixture of racemic diastereomers (1.06 g, 3.70 mmol).

ESI-MS; m/z: 309[M+Na]⁺

¹H-NMR (400 MHz, CDCl₃)

δ (ppm): 1.51-1.90 (m, 6H), 2.35 (s, 1.5H), 2.43 (s, 1.5H), 3.19-3.29 (m, 1H), 3.45-3.64 (m, 2H), 3.98-4.11 (m, 1H), 4.88 (t, J=3.4 Hz, 0.5H), 4.95 (d, J=5.1 Hz, 0.5H), 5.01 (dd, J=11.6, 2.8 Hz, 0.5H), 5.16 (d, J=11.7 Hz, 0.5H), 6.74-6.81 (m, 2H)

(5) Synthesis of 2,2,5-trifluoro-7-methyl-2,3-dihydro-1H-inden-1-ol

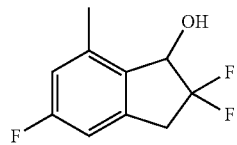

To a solution of the product obtained in Example 12-(4) (1.06 g, 3.70 mmol) in MeOH (10 ml) was added PPTS (46 mg, 0.185 mmol). And the reaction mixture was stirred for 1 hour at 60° C. After cooling to room temperature, saturated NaHCO$_3$ was added to the reaction mixture and the mixture was extracted with AcOEt. The organic layer was washed with brine and dried over anhydrous Na$_2$SO$_4$. The insoluble matter was filtered off and the filtrate was evaporated in vacuo. The residue was purified by silicagel flash column chromatography (Yamazen HI-FLASH™ column M size, 10 mL/min, gradient 5% to 25% AcOEt in n-heptane) to afford the title compound (692 mg, 3.42 mmol).

$^1$H-NMR (400 MHz, CDCl$_3$)

δ (ppm): 2.23 (dd, J=5.7, 2.5 Hz, 1H), 2.42 (s, 3H), 3.30 (td, J=16.8, 5.2 Hz, 1H), 3.50 (td, J=16.8, 11.6 Hz, 1H), 5.05 (dd, J=12.1, 5.1 Hz, 1H), 6.77 (d, J=8.2 Hz, 1H), 6.82 (d, J=10.2 Hz, 1H).

(6) Synthesis of 1-Azido-2,2,5-trifluoro-7-methyl-2,3-dihydro-1H-inden

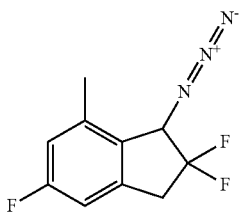 [SMILES: Cc1cc(F)cc2c1C(N=[N+]=[N-])C(F)(F)C2]

To a solution of the product obtained in Example 12-(5) (692 mg, 3.42 mmol) and TEA (1.43 ml, 10.3 mmol) in DCM (10 ml) was added chloromethanesulfonyl chloride (765 mg, 5.13 mmol) at 0° C. And the reaction mixture was stirred for 2 hours at room temperature. To the reaction mixture was added saturated NaHCO$_3$ and the mixture was extracted with diethyl ether. The organic layer was successively washed with 1N HCl and brine then dried over anhydrous Na$_2$SO$_4$. After filtration, the filtrate was evaporated in vacuo. To a solution of the residue in DMF (10 ml) was added sodium azide (442 mg, 6.80 mmol) at room temperature, and the mixture was stirred for 2 hours at 70° C. After cooling to room temperature, the mixture was partitioned between diethyl ether and H$_2$O. The aqueous layer was extracted with diethyl ether. The combined organic layer was washed with brine and dried over anhydrous Na$_2$SO$_4$.

After filtration, the filtrate was evaporated in vacuo.

The residue was purified by silicagel flash column chromatography (Yamazen HI-FLASH™ column M size, 10 mL/min, gradient 10% to 30% AcOEt in n-heptane) to afford the title compound (320 mg, 1.41 mmol). $^1$H-NMR (400 MHz, CDCl$_3$)

δ (ppm): 2.41 (s, 3H), 3.30-3.56 (m, 2H), 4.74 (d, J=13.3 Hz, 1H), 6.81 (d, J=7.8 Hz, 1H), 6.86 (d, J=9.4 Hz, 1H).

(7) Synthesis of 2,2,5-trifluoro-7-methyl-2,3-dihydro-1H-inden-1-amine

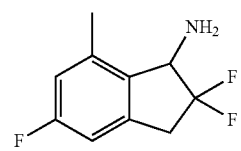

To a solution of the product obtained in Example 12-(6) (320 mg, 1.41 mmol) in water (1 ml) and THF (5 ml) was added triphenylphosphine (554 mg, 2.11 mmol) at room temperature, and the mixture was stirred for 2 hours at 80° C. After cooling to room temperature, the mixture was partitioned between AcOEt and 1N HCl. The obtained aqueous layer was basified with 5N NaOH, and extracted with AcOEt for 3 times. The combined extract was dried over anhydrous Na$_2$SO$_4$. After filtration, the filtrate was concentrated in vacuo to afford the title compound (180 mg, 0.895 mmol).

ESI-MS; m/z: 202[M+H]$^+$ (8) Synthesis of tert-butyl N-(2,2,5-trifluoro-7-methyl-2,3-dihydro-1H-inden-1-yl)sulfamoylcarbamate

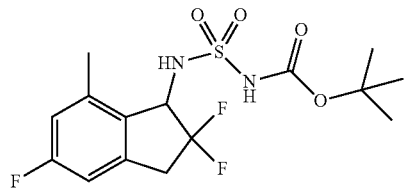 [SMILES: Cc1cc(F)cc2c1C(NS(=O)(=O)NC(=O)OC(C)(C)C)C(F)(F)C2]

To a solution of the product in Example 12-(7) (180 mg, 0.895 mmol) in DCM (10 mL) were added [(tert-Butoxy)carbonyl]{[4-(dimethyliminio)pyridin-1(4H)-yl]sulfonyl}amide (297 mg, 0.984 mmol) and TEA (0.374 mL, 2.68 mmol) at room temperature. The resulting mixture was heated under reflux for 65.5 hours. After cooling to room temperature, the mixture was partitioned between AcOEt and 1N HCl. The organic layer was dried over anhydrous Na$_2$SO$_4$ and evaporated in vacuo to afford the title compound (257 mg, 0.676 mmol).

ESI-MS; m/z: 403 [M±Na]$^+$ (9) Synthesis of N-[(1S)-2,2,5-trifluoro-7-methyl-2,3-dihydro-1H-inden-1-yl]sulfamide

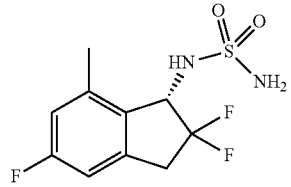 [SMILES: Cc1cc(F)cc2c1[C@H](NS(N)(=O)=O)C(F)(F)C2]

To a solution of the product in Example 12-(8) (257 mg, 0.676 mmol) in MeOH (4 mL) was added 4N HCl in AcOEt (3.38 ml, 13.5 mmol) at room temperature and stirred at room temperature for 14 hours. The solvent was evaporated in vacuo and the residue was purified by silicagel column chromatography (AcOEt) to afford the title compound (162 mg, 0.578 mmol) as a racemate.

Optical resolution of the obtained racemate (162 mg, 0.578 mmol) was conducted by HPLC (CHIRALPAK™ IF, 20 mm I.D.×250 mm, 10% EtOH in n-hexane, 10 mL/min) to afford the title (S)-isomer (71 mg, 0.253 mmol, 98% ee) as white solids, which was eluted second with retention time of 30 min among the 2 optical isomers.

ESI-MS; m/z: 303[M+Na]$^+$ $^1$H-NMR (400 MHz, DMSO-d$_6$)

δ (ppm): 2.37 (s, 3H), 3.20-3.31 (m, 1H), 3.38-3.64 (m, 1H), 4.79 (dd, J=14.3, 8.8 Hz, 1H), 6.77 (s, 2H), 6.90-7.03 (m, 2H), 7.51 (d, J=9.0 Hz, 1H).

Example 13

Synthesis of N-[(1S*)-2,2,4-trifluoro-7-methyl-2,3-dihydro-1H-inden-1-yl]sulfamide

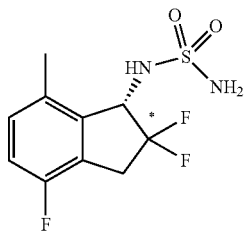

(1)

Synthesis of 7-bromo-2,2,4-trifluoro-2,3-dihydro-1H-inden-1-one

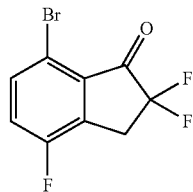 [SMILES: O=C1c2c(Br)ccc(F)c2CC1(F)F]

The title compound (2.94 g, 11.1 mmol) was obtained from 7-bromo-4-fluoro-1-indanone (CASNo. 881189-73-7, 4.00 g, 17.5 mmol) by a similar method as described in Example 1-(1) and 1-(2).

$^1$H-NMR (400 MHz, CDCl$_3$)

δ ppm 3.54 (t, J=12.7 Hz, 2H), 7.30 (t, J=8.6 Hz, 1H), 7.64 (dd, J=8.6, 4.3 Hz, 1H).

(2) Synthesis of 7-bromo-2,2,4-trifluoro-2,3-dihydro-1H-inden-1-ol

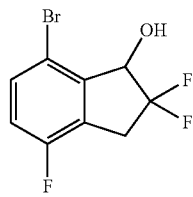 [SMILES: OC1c2c(Br)ccc(F)c2CC1(F)F]

The title compound (1.96 g, 7.32 mmol) was obtained from the product obtained in Example 13-(1) (1.94 g, 7.32 mmol) by a similar method as described in Example 11-(3).

$^1$H-NMR (400 MHz, CDCl$_3$)

δ ppm 2.51 (dd, J=4.5, 1.8 Hz, 1H), 3.43-6.22 (m, 2H), 5.10 (dd, J=12.1, 4.5 Hz, 1H), 6.98 (t, J=8.6 Hz, 1H), 7.44 (dd, J=8.6, 4.5 Hz, 1H).

(3) Synthesis of 2-[(2,2,4-trifluoro-7-methyl-2,3-dihydro-1H-inden-1-yl)oxy]tetrahydro-2H-pyran

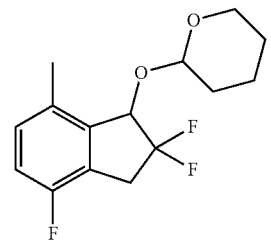 [SMILES: Cc1ccc(F)c2c1C(OC1CCCCO1)C(F)(F)C2]

The title compound (2.42 g, 6.92 mmol) was obtained as about a 1:1 mixture of racemic diastereomers from the product obtained in Example 13-(2) (1.95 g, 7.30 mmol) by a similar method as described in Example 12-(3) and 12-(4).

$^1$H-NMR (400 MHz, CDCl$_3$)

δ (ppm): 1.51-1.81 (m, 6H), 3.36-3.65 (m, 3H), 4.06-4.20 (m, 1H), 5.05 (d, J=12.1 Hz, 0.5H), 5.11 (brs, 0.5H), 5.17 (d, J=10.5 Hz, 0.5H), 5.23-5.25 (m, 0.5H), 6.95 (td, J=8.6, 6.1 Hz, 1H), 7.43 (dt, J=8.6, 4.3 Hz, 1H).

(4) Synthesis of 2,2,4-trifluoro-7-methyl-2,3-dihydro-1H-inden-1-ol

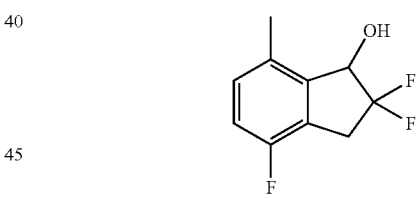

The title compound (321 mg, 1.59 mmol) was obtained from the product obtained in Example 13-(3) (800 mg, 2.28 mmol) by a similar method as described in Example 12-(5).

$^1$H-NMR (400 MHz, CDCl$_3$)

δ (ppm): 2.55 (dd, J=6.2, 2.7 Hz, 1H), 2.39 (s, 3H), 3.33-3.55 (m, 2H), 5.07-5.12 (m, 1H), 6.95 (t, J=8.0 Hz, 1H), 7.08 (dd, J=8.0, 4.5 Hz, 1H).

(5) Synthesis of 2,2,4-trifluoro-7-methyl-2,3-dihydro-1H-inden-1-amine

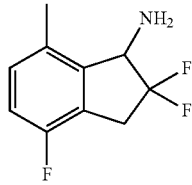

The title compound (85 mg, 0.422 mmol) was obtained from the product obtained in Example 13-(4) (321 mg, 1.59 mmol) a similar method as described in Example 12-(6) and 12-(7).

¹H-NMR (400 MHz, CDCl₃)

δ (ppm): 1.43 (brs, 2H), 2.40 (s, 3H), 3.31-3.51 (m, 2H), 4.38 (d, J=14.4 Hz, 1H), 6.90 (t, J=8.4 Hz, 1H), 7.04 (dd, J=8.4, 4.9 Hz, 1H).

(6) Synthesis of N-[(1S*)-2,2,4-trifluoro-7-methyl-2,3-dihydro-1H-inden-1-yl]sulfamide

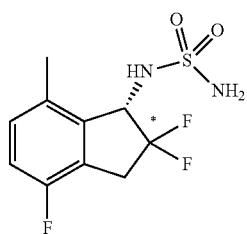 [SMILES: Cc1ccc(F)c2c1[C@H](NS(N)(=O)=O)C(F)(F)C2]

To a solution of the product obtained in Example 13-(5) (85 mg, 0.422 mmol) in DCM (4 mL) were added TEA (177 μL, 1.27 mmol) and sulfamoyl chloride (4 ml, 0.159M solution in DCM) at 0° C. and the reaction mixture was stirred for 1 hour at room temperature. The reaction mixture was acidified with 2N HCl, and extracted with AcOEt. The organic layer was washed with brine and dried over anhydrous Na₂SO₄. After filtration, the filtrate was concentrated in vacuo. The residue was purified by flash silicagel column chromatography (Yamazen HI-FLASH™ column M size, 10 mL/min, gradient 20% to 50% AcOEt in n-heptane) to afford the title compound (69 mg, 0.246 mmol).

ESI-MS; m/z: 303[M+Na]⁺

Optical resolution of the obtained racemate (48 mg, 0.171 mmol) was conducted by HPLC (CHIRALPAK™ IC, 20 mm I.D.×250 mm, 10% EtOH in n-hexane, 10 mL/min) to afford the title enantiomer (8 mg, 0.029 mmol, >99% ee), which was eluted second among the 2 optical isomers.

¹H-NMR (400 MHz, DMSO-d₆)

δ (ppm): 2.37 (s, 3H), 3.20-3.31 (m, 1H), 3.38-3.64 (m, 1H), 4.79 (dd, J=14.3, 8.8 Hz, 1H), 6.77 (s, 2H), 6.90-7.03 (m, 2H), 7.51 (d, J=9.0 Hz, 1H).

Example 14

Synthesis of N-[(1S*)-7-(difluoromethyl)-2,2-difluoro-2,3-dihydro-1H-inden-1-yl]sulfamide

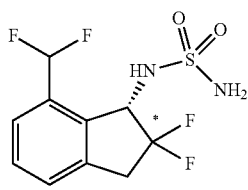

(1)

Synthesis of 7-bromo-2,2-difluoro-2,3-dihydro-1H-inden-1-one

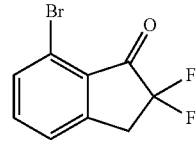 [SMILES: O=C1c2c(Br)cccc2CC1(F)F]

The title compound (1.96 g, 7.95 mmol) was obtained from 7-bromo-1-indanone (CAS No. 125114-77-4, 2.00 g, 9.48 mmol) by a similar method as described in Example 1-(1) and 1-(2).

¹H-NMR (400 MHz, CDCl₃)

δ ppm 3.53 (t, J=12.9 Hz, 2H), 7.43 (d, J=7.8 Hz, 1H), 7.55 (t, J=7.8 Hz, 1H), 7.65 (t, J=7.8 Hz, 1H).

(2) Synthesis of 7-bromo-2,2-difluoro-2,3-dihydro-1H-inden-1-ol

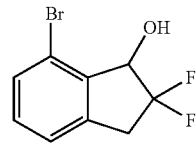

The title compound (1.98 g, 7.95 mmol) was obtained from the product obtained in Example 14-(1) (1.96 g, 7.95 mmol) by a similar method as described in Example 11-(3).

¹H-NMR (400 MHz, CDCl₃)

δ (ppm): 2.46 (dd, J=4.5, 1.8 Hz, 1H), 3.39 (td, J=16.9, 3.3 Hz, 1H), 3.56-3.66 (m, 1H), 5.11 (dd, J=12.3, 4.5 Hz, 1H), 7.20-7.25 (m, 2H), 7.46 (dd, J=6.6, 1.6 Hz, 1H).

(3) Synthesis of 2-[(7-bromo-2,2-difluoro-2,3-dihydro-1H-inden-1-yl)oxy]tetrahydro-2H-pyran

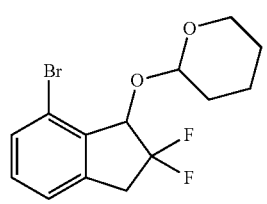 [SMILES: FC1(F)Cc2cccc(Br)c2C1OC1CCCCO1]

The title compound (2.53 g, 7.60 mmol) was obtained as about a 1:1 mixture of racemic diastereomers from the product obtained in Example 14-(2) (1.98 g, 7.95 mmol) by a similar method as described in Example 12-(3).

¹H-NMR (400 MHz, CDCl₃)

δ (ppm): 1.50-1.84 (m, 6H), 3.26-3.39 (m, 1H), 3.53-3.68 (m, 2H), 4.07-4.23 (m, 1H), 5.04-5.25 (m, 2H), 7.18-7.23 (m, 2H), 7.45 (t, J=5.7 Hz, 1H).

(4) Synthesis of 2,2-difluoro-3-[(tetrahydro-2H-pyran-2-yl)oxy]-2,3-dihydro-1H-inden-4-carbaldehyde

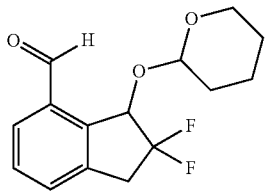 [SMILES: O=Cc1cccc2c1C(OC1CCCCO1)C(F)(F)C2]

The product obtained in Example 14-(3) (2.00 g, 6.00 mmol) was dissolved in THF (30 ml) and the solution was cooled in a dry ice-EtOH bath. n-Butyl lithium (2.68 ml, 2.69 M in hexane) was added dropwise and the mixture was stirred for 20 minutes under cooling. Then DMF (0.70 ml, 9.00 mmol) was added to the reaction mixture and the mixture was stirred for 3 hours at room temperature. To the reaction mixture was added water, and the mixture was extracted with AcOEt. The organic layer was washed with brine and dried over anhydrous $Na_2SO_4$. After filtration, the filtrate was concentrated in vacuo. The residue was purified by silicagel flash column chromatography (Yamazen HI-FLASH™ column L size, 20 mL/min, gradient 5% to 33% AcOEt in n-heptane) to afford the title compound (1.09 g, 3.86 mmol) as about a 1:1 mixture of racemic diastereomers.

$^1$H-NMR (400 MHz, $CDCl_3$)

δ (ppm): 1.49-1.85 (m, 6H), 3.28-3.41 (m, 1H), 3.51-3.65 (m, 2H), 3.87-4.10 (m, 1H), 5.02-5.04 (m, 1H), 5.51 (dd, J=11.7, 2.0 Hz, 0.5H), 5.71 (dd, J=11.1, 1.8 Hz, 0.5H), 7.47-7.56 (m, 2H), 7.80-7.88 (m, 1H), 10.19 (s, 0.5H), 10.48 (s, 0.5H).

(5) Synthesis of 2-[(7-difluoromethyl-2,2-difluoro-2,3-dihydro-1H-inden-1-yl)oxy]tetrahydro-2H-pyran

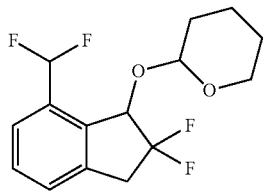 [SMILES: FC(F)c1cccc2c1C(OC1CCCCO1)C(F)(F)C2]

To a solution of the product obtained in Example 14-(4) (1.09 g, 3.87 mmol) in DCM (19 ml) were added BAST (2.14 ml, 11.6 mmol) and water (6.96 µl, 0.386 mmol) at room temperature. The mixture was stirred for 15 hours at room temperature.

To the reaction mixture was added saturated aqueous $NaHCO_3$, and the mixture was extracted with AcOEt. The organic layer was washed with brine and dried over anhydrous $Na_2SO_4$. After filtration, the filtrate was concentrated in vacuo. The residue was purified by silicagel flash column chromatography (Yamazen HI-FLASH™ column L size, 20 mL/min, gradient 5% to 25% AcOEt in n-heptane) to afford the title compound (747 mg, 2.46 mmol) as about a 1:1 mixture of racemic diastereomers.

$^1$H-NMR (400 MHz, $CDCl_3$)

δ (ppm): 1.48-1.97 (m, 6H), 3.17-3.75 (m, 3H), 3.95-4.18 (m, 1H), 4.95 (brs, 1H), 5.23-5.28 (m, 0.5H), 5.42 (d, J=10.9 Hz, 0.5H), 6.79-7.28 (m, 1H), 7.34-7.61 (m, 3H).

(6) Synthesis of 7-(difluoromethyl)-2,2-difluoro-2,3-dihydro-1H-inden-1-ol

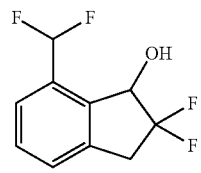 [SMILES: OC1c2c(cccc2C(F)F)CC1(F)F]

To a solution of the product obtained in Example 14-(5) (747 mg, 2.46 mmol) in MeOH (12 ml) was added PPTS (61.7 mg, 0.245 mmol) at room temperature. The reaction mixture was stirred for 1 hour at 60° C., and then cooled to room temperature. To the reaction mixture was added saturated aqueous $NaHCO_3$ and the mixture was extracted with AcOEt. The organic layer was washed with brine and dried over anhydrous $Na_2SO_4$. After filtration, the filtrate was evaporated in vacuo. The residue was purified by silicagel flash column chromatography (Yamazen HI-FLASH™ column M size, 10 mL/min, gradient 5% to 67% AcOEt in n-heptane) to afford the title compound (459 mg, 2.09 mmol).

$^1$H-NMR (400 MHz, $CDCl_3$)

δ (ppm): 2.47 (dd, J=6.0, 2.9 Hz, 1H), 3.33-3.59 (m, 2H), 5.34 (dt, J=11.5, 6.0 Hz, 1H), 7.04 (t, J=55.6 Hz, 1H), 7.37 (dd, J=7.6, 0.8 Hz, 1H), 7.45 (t, J=7.6 Hz, 1H), 7.50 (d, J=7.6 Hz, 1H).

(7) Synthesis of 7-(difluoromethyl)-2,2-difluoro-2,3-dihydro-1H-inden-1-amine

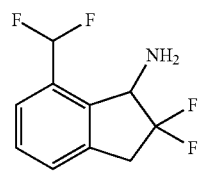 [SMILES: NC1c2c(cccc2C(F)F)CC1(F)F]

The title compound (185 mg, 0.388 mmol) was obtained from the product obtained in Example 14-(6) (160 mg, 0.727 mmol) by a similar method as described in Example 12-(6) and 12-(7).

ESI-MS; m/z: 200[M+H]$^+$ $^1$H-NMR (400 MHz, $CDCl_3$)

δ (ppm): 1.56 (brs, 2H), 3.29-3.54 (m, 2H), 4.62 (dd, J=12.7, 6.8 Hz, 1H), 7.32 (d, J=8.0 Hz, 1H), 7.36 (t, J=56.0 Hz, 1H), 7.39 (t, J=8.0 Hz, 1H), 7.53 (d, J=8.0 Hz, 1H).

(8) Synthesis of N-[(1S*)-7-(difluoromethyl)-2,2-difluoro-2,3-dihydro-1H-inden-1-yl]sulfamide

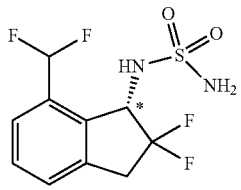

The title compound (30 mg, 0.176 mmol) was obtained as a racemate from the product obtained in Example 14-(7) (85 mg, 0.388 mmol) by a similar method as described in Example 1-(4) and 1-(5).

ESI-MS; m/z: 321[M+Na]+
$^1$H-NMR (400 MHz, DMSO-d$_6$)
δ (ppm): 3.37-3.62 (m, 2H), 5.01-5.07 (m, 1H), 6.91 (s, 2H), 7.29 (t, J=55.6 Hz, 1H), 7.47 (d, J=7.6 Hz, 1H), 7.52 (d, J=7.6 Hz, 1H), 7.56 (d,
J=7.6 Hz, 1H), 7.81 (d, J=9.4 Hz, 1H).

Optical resolution of the obtained racemate (30 mg, 0.176 mmol) was conducted by HPLC (CHIRALPAK™ IA, 20 mm I.D.×250 mm, 15% EtOH in n-hexane, 10 mL/min) to afford the title enantiomer (8 mg, 0.101 mmol, >99% ee), which was eluted second among the 2 optical isomers.

As a result of analysis by DAICEL CHIRALPAK™ IA (4.6 mm I.D.×150 mm, 15% EtOH in n-hexane, 1 mL/min), the optical isomer showed retention time of 12 min.

Example 15

Synthesis of N-[(1R*,2R*)-2,4,7-trifluoro-2,3-dihydro-1H-inden-1-yl]sulfamide

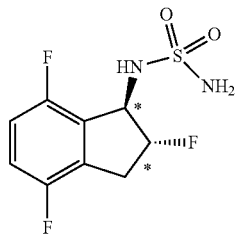 [SMILES: NS(=O)(=O)N[C@@H]1c2c(F)ccc(F)c2C[C@H]1F]

(1) Synthesis of 2,4,7-trifluoro-2,3-dihydro-1H-inden-1-one

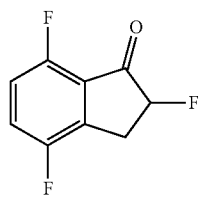 [SMILES: O=C1c2c(F)ccc(F)c2CC1F]

Selectfluor™ (11.7 g, 33.0 mmol) was added to a solution of 4,7-difluoro-1-indanone (CAS No. 130408-16-1, 5.04 g, 30.0 mmol) in MeOH (100 mL) at room temperature. The mixture was refluxed for 4 hours. After cooling to room temperature, 5 N HCl (5 mL) was added to the mixture, and then the mixture was stirred at room temperature for 1 hour. After the reaction mixture was concentrated in vacuo, the residue was partitioned between AcOEt and saturated aqueous NaHCO$_3$.

The organic layer was washed with brine, dried over MgSO$_4$, and the solvent was evaporated in vacuo to afford the title compound (5.56 g, 29.9 mmol).
$^1$H-NMR (400 MHz, CDCl$_3$)
δ (ppm) 3.11-3.26 (m, 1H) 3.62-3.73 (m, 1H) 5.23 (ddd, J=50.4, 7.8, 4.1 Hz, 1H), 7.03-7.09 (m, 1H) 7.32-7.37 (m, 1H).

(2) Synthesis of N-[(1R*,2R*)-2,4,7-trifluoro-2,3-dihydro-1H-inden-1-yl]sulfamide

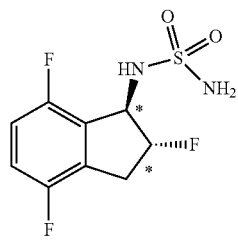

Ammonium acetate (7.71 g, 100 mmol) and MgSO$_4$ (12.0 g, 100 mmol) were added to a solution of the compound (931 mg, 5.00 mmol) obtained in Example 15-(1) in isopropanol (30 mL) at room temperature. The mixture was heated under reflux for 2 hours. Sodium cyanoborohydride (943 mg, 15.0 mmol) was added to the reaction mixture and refluxed for 5 hours. After cooling to room temperature, the reaction mixture was concentrated in vacuo.

Diethyl ether and 2N HCl were added to the residue, and the mixture was partitioned. The aqueous layer was neutralized with 2N NaOH and extracted with AcOEt. The organic layer was washed with brine, dried over MgSO$_4$. The solvent was evaporated in vacuo and the residue was dried to afford (1RS,2RS)-2,4,7-trifluoro-2,3-dihydro-1H-inden-1-amine and (1RS,2SR)-2,4,7-trifluoro-2,3-dihydro-1H-inden-1-amine as a diastereomer mixture (170 mg, 0.91 mmol).

To a solution of the diastereomer mixture (168 mg, 0.90 mmol) in DCM (10 mL) were added [(tert-Butoxy)carbonyl]{[4-(dimethyliminio)pyridin-1(4H)-yl]sulfonyl}amide (353 mg, 1.17 mmol) and TEA (0.13 mL, 0.90 mmol) at room temperature. The solution was stirred at room temperature for 15 hours. The reaction mixture was diluted with AcOEt and 1N HCl. Then the layers were separated, and the organic layer was dried over anhydrous Na$_2$SO$_4$ and evaporated in vacuo. The residue was purified by silicagel column chromatography (20%-30%, AcOEt in n-heptane) to afford (1RS,2RS)-[tert-butyl N-(2,4,7-trifluoro-2,3-dihydro-1H-inden-1-yl) sulfamoylcarbamate] and (1RS,2SR)-[tert-butyl N-(2,4,7-trifluoro-2,3-dihydro-1H-inden-1-yl) sulfamoylcarbamate] as a diastereomer mixture (190 mg, 0.52 mmol). To a solution of the diastereomer mixture (183 mg, 0.50 mmol) in MeOH (2 mL) was added 4N HCl in AcOEt (2 ml) at room temperature and stirred at room temperature for 16 hours. The solvent was evaporated in vacuo and the residue was dried to afford the title compound as a mixture. The mixture obtained was separated by HPLC (CHIRALPAK™ IA, 20 mm I.D.×250 mm, 10 mL/min, 20% EtOH in n-hexane) to afford the title compound, that was eluted second among the 4 optically active compounds with retention time of 14 minutes (76 mg, 0.267 mmol; >99% ee).

ESI-MS m/z: 289[M+Na]+

¹H NMR (400 MHz, CDCl₃)

δ (ppm): 3.22 (dd, J=24.8, 18.0 Hz, 1H), 3.39-3.52 (m, 1H), 4.58 (brs, 1H), 4.73 (brs, 2H), 5.15 (d, J=16.6 Hz, 1H), 5.58-5.61 (m, 1H), 6.93-7.01 (m, 1H), 7.02-7.09 (m, 1H).

Example 16

Synthesis of (−)-N-[(1R*,2R*)-7-chloro-2,4-difluoro-2,3-dihydro-1H-inden-1-yl]sulfamide (16a) and (+)-N-[(1R*,2R*)-7-chloro-2,4-difluoro-2,3-dihydro-1H-inden-1-yl]sulfamide (16b)

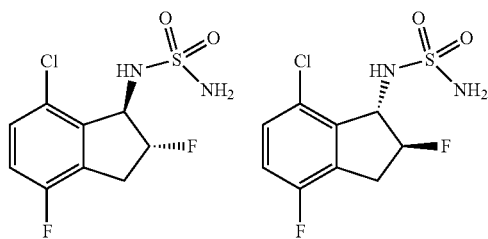 [SMILES: NS(=O)(=O)N[C@@H]1c2c(Cl)ccc(F)c2C[C@H]1F ; NS(=O)(=O)N[C@H]1c2c(Cl)ccc(F)c2C[C@@H]1F]

(1) Synthesis of 7-chloro-2,4-difluoro-2,3-dihydro-1H-inden-1-one

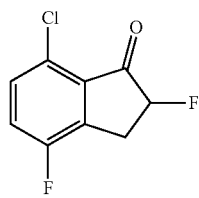

The title compound (181 mg, 0.637 mmol) was obtained from 7-chloro-4-fluoro-1-indanone (CAS No. 881190-28-9, 1.85 g, 10.0 mmol) by a similar method as described in Example 15-(1).

¹H-NMR (400 MHz, CDCl₃)

δ (ppm): 3.09-3.22 (m, 1H), 3.60-3.70 (m, 1H), 5.25 (ddd, J=50.8, 8.0, 4.5 Hz, 1H), 7.27-7.31 (m, 1H), 7.36-7.39 (m, 1H).

(2) Synthesis of (−)-N-[(1R*,2R*)-7-chloro-2,4-difluoro-2,3-dihydro-1H-inden-1-yl]sulfamide (16a) and (+)-N-[(1R*,2R*)-7-chloro-2,4-difluoro-2,3-dihydro-1H-inden-1-yl]sulfamide (16b)

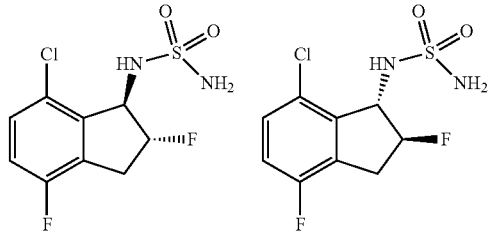 [SMILES: NS(=O)(=O)N[C@@H]1c2c(Cl)ccc(F)c2C[C@H]1F ; NS(=O)(=O)N[C@H]1c2c(Cl)ccc(F)c2C[C@@H]1F]

A mixture of 4 isomers was obtained from the product (405 mg, 2.00 mmol) obtained in Example 16-(1) by a similar method as described in Example 15-(2). The mixture was separated by HPLC (CHIRALPAK™ IF, 20 mm I.D.×250 mm, 10 mL/min, 20% EtOH in hexane) to afford the (−)-form of title compound (8.2 mg, 0.029 mmol; >99% ee), that was eluted first with retention time of 9 min, and the (+)-form of title compound (8.3 mg, 0.029 mmol; >99% ee), that was eluted second with retention time of 12 min among the 4 optically active compounds, respectively.

The property values of the (−)-form of title compound are as follows.

ESI-MS; m/z 305, 307[M+Na]+.

¹H-NMR (400 MHz, CDCl₃) δ (ppm): 3.21 (dd, J=25.4, 18.4 Hz, 1H), 3.40-3.56 (m, 1H), 4.73 (brs, 3H), 5.03 (d, J=16.2 Hz, 1H), 5.56 (dd, J=49.2, 4.7 Hz, 1H), 7.05 (t, J=8.4 Hz, 1H), 7.23-7.29 (m, 1H).

The property values of the (+)-form of title compound were the same as those of the (−)-form.

ESI-MS; m/z305, 307[M+Na]+.

1H-NMR (400 MHz, CDCl₃) δ (ppm): 3.21 (dd, J=25.4, 18.4 Hz, 1H), 3.40-3.56 (m, 1H), 4.73 (brs, 3H), 5.03 (d, J=16.2 Hz, 1H), 5.56 (dd, J=49.2, 4.7 Hz, 1H), 7.05 (t, J=8.4 Hz, 1H), 7.23-7.29 (m, 1H).

Example 17

Synthesis of (−)-N-[(1R*,2R*)-7-chloro-2,5-difluoro-2,3-dihydro-1H-inden-1-yl]sulfamide

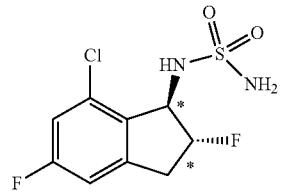

A mixture of 4 isomers (2 racemic diastereomers) was obtained from the product (1.06 g, 5.23 mmol) obtained in Example 6-(1) by a similar method as described in Example 15-(2). The mixture was purified by silicagel column chromatography (WAKO, Presep™ Silicagel (HC-N), size: 3 L, 60 mL/min, 30%-60%, AcOEt in n-heptane) to afford the title compound as a racemate (177 mg, 0.626 mmol). The obtained racemate (175 mg, 0.619 mmol) was separated by HPLC (CHIRALPAK™ IB, 20 mm I.D.×250 mm, 10 mL/min, 10% EtOH in n-hexane) to afford the (−)-form of title compound (67 mg, 0.237 mmol; 99% ee), that was eluted second with retention time of 40 min among the 2 isomers.

ESI-MS; m/z305 [M+Na]+.

1H-NMR (400 MHz, CDCl₃) δ (ppm): 3.21 (dd, J=25.4, 18.4 Hz, 1H), 3.40-3.56 (m, 1H), 4.73 (brs, 3H), 5.03 (d, J=16.2 Hz, 1H), 5.56 (dd, J=49.2, 4.7 Hz, 1H), 7.05 (t, J=8.4 Hz, 1H), 7.23-7.29 (m, 1H).

Example 18

Synthesis of (+)-N-[(1R*,2R*)-4-chloro-7-fluoro-2-methoxy-2,3-dihydro-1H-inden-1-yl]sulfamide

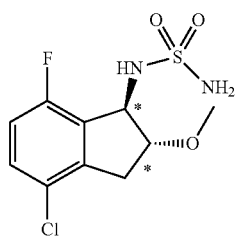 [SMILES: CO[C@@H]1Cc2c(Cl)ccc(F)c2[C@H]1NS(N)(=O)=O]

(1) Synthesis of (1RS,2RS)-2-bromo-4-chloro-7-fluoro-2,3-dihydro-1H-inden-1-ol

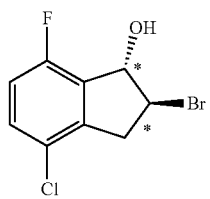 [SMILES: O[C@H]1c2c(F)ccc(Cl)c2C[C@@H]1Br]

To a solution of 4-chloro-7-fluoro-2,3-dihydro-1H-inden-1-one (CAS No. 1260018-63-0, 900 mg, 4.88 mmol) in MeOH (30 mL) was added sodium borohydride (221 mg, 5.85 mmol) at room temperature. The reaction mixture was stirred for 20 minutes at room temperature. To the reaction was added 2N HCl, AcOEt and water at 0° C. The layers were separated. The organic layer was washed with brine and dried over MgSO$_4$, then the solvent was evaporated in vacuo. To a solution of the residue in toluene (50 ml) was added p-toluenesulfonic acid monohydrate (100 mg, 0.53 mmol) and the reaction mixture was refluxed for 20 minutes. After cooling to room temperature, the reaction mixture was passed through NH silicagel and evaporated in vacuo. To a solution of the residue in THF (30 ml) and water (10 ml) was added NBS (842 mg, 4.73 mmol) and the reaction mixture was stirred for 20 hours at room temperature. AcOEt and brine were added to the mixture, and the layers were separated. The organic layer was successively washed with saturated aqueous Na$_2$S$_2$O$_3$ and brine and then dried over MgSO$_4$. The solvent was evaporated in vacuo. The residue was purified by silicagel flash column chromatography (Yamazen HI-FLASH™ column L size, 40 mL/min, gradient 0% to 40% AcOEt in n-heptane) to afford the title compound (675 mg, 2.54 mmol).

$^1$H-NMR (400 MHz, CDCl$_3$)

δ (ppm): 2.43 (d, J=4.5 Hz, 1H), 3.28 (dd, J=17.8, 4.5 Hz, 1H), 3.78 (dd, J=17.8, 6.5 Hz, 1H), 4.41-4.45 (m, 1H), 5.60-5.62 (m, 1H), 6.92-6.97 (m, 1H), 7.29 (dd, J=8.8, 4.3 Hz, 1H).

(2) Synthesis of (1RS, 2RS)-1-Azido-4-chloro-7-fluoro-2,3-dihydro-1H-inden-2-ol

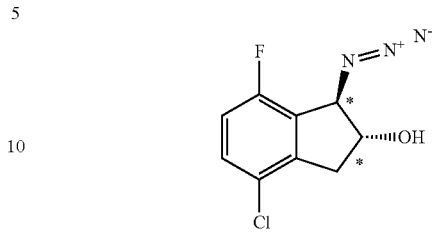

To a solution of the product obtained in Example 18-(1) (675 mg, 2.54 mmol) in THF (10 ml) was added potassium hydroxide (357 mg, 6.36 mmol) at room temperature. And the reaction mixture was stirred for 2 hours at room temperature. AcOEt and brine were added to the mixture, and the layers were separated. The organic layer was dried over MgSO$_4$ and evaporated in vacuo. To a solution of the residue in EtOH (12 ml) and water (4 ml) were added ammonium chloride (204 mg, 3.81 mmol) and sodium azide (248 mg, 3.81 mmol) at room temperature. The mixture was refluxed for 2 hours. After cooling to room temperature, the mixture was partitioned between AcOEt and brine. The organic layer was dried over MgSO$_4$ and evaporated in vacuo. The residue was purified by silicagel flash column chromatography (Yamazen HI-FLASH™ column L size, 40 mL/min, gradient 0% to 40% AcOEt in n-heptane) to afford the title compound (452 mg, 1.99 mmol).

$^1$H-NMR (400 MHz, CDCl$_3$)

δ (ppm): 2.91 (d, J=17.2, 3.7 Hz, 1H), 3.36-3.42 (m, 1H), 4.50-4.53 (m, 1H), 4.98 (d, J=2.9 Hz, 1H), 6.95-6.99 (m, 1H), 7.30 (dd, J=8.6, 4.3 Hz, 1H).

(3) Synthesis of t-butyl [(1RS,2RS)-4-chloro-7-fluoro-2-hydroxy-2,3-dihydro-1H-inden-1-yl]carbamate

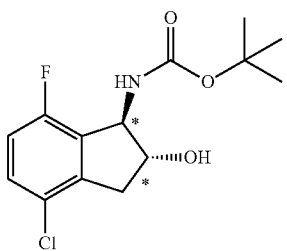 [SMILES: CC(C)(C)OC(=O)N[C@@H]1c2c(F)ccc(Cl)c2C[C@H]1O]

To a solution of the product obtained in Example 18-(2) (452 mg, 1.99 mmol) in THF (6 ml) and water (2 ml) was added triphenylphosphine (781 mg, 2.99 mmol) at room temperature. And the reaction mixture was refluxed for 2 hours. AcOEt and 2N HCl were added to the mixture, and the layers were separated. The aqueous layer was basicified with 5N sodium hydroxide and was extracted with DCM. The extract was dried over MgSO$_4$ and evaporated in vacuo.

The residue was dissolved in MeOH (5 ml) and Boc$_2$O (650 mg, 2.99 mmol) was added to the solution. Then the solvent was evaporated in vacuo.

The residue was purified by silicagel flash column chromatography (Yamazen HI-FLASH™ column L size, 40 mL/min, gradient 0% to 60% AcOEt in n-heptane) to afford the title compound (313 mg, 1.04 mmol).

ESI-MS; m/z: 324[M+Na]$^+$ (4) Synthesis of t-butyl [(1RS,2RS)-4-chloro-7-fluoro-2-methoxy-2,3-dihydro-1H-inden-1-yl]carbamate

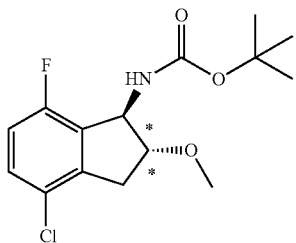 [SMILES: CO[C@@H]1Cc2c(Cl)ccc(F)c2[C@H]1NC(=O)OC(C)(C)C]

To a solution of the product obtained in Example 18-(3) (313 mg, 1.04 mmol) in THF (5 ml) and 50% aqueous sodium hydroxide solution (5 ml) were added benzyltriethylammonium chloride (23 mg, 0.10 mmol) and iodomethane (294 mg, 2.08 mmol) at room temperature. And the reaction mixture was stirred for 14 hours at room temperature. AcOEt and brine were added to the mixture, and the layers were separated. The organic layer was dried over MgSO$_4$ and evaporated in vacuo. The residue was purified by silicagel flash column chromatography (Yamazen HI-FLASH™ column L size, 40 mL/min, gradient 0% to 40% AcOEt in n-heptane) to afford the title compound (321 mg, 1.02 mmol).

ESI-MS; m/z: 338[M+Na]$^+$ (5) Synthesis of (+)-N-[(1R*,2R*)-4-chloro-7-fluoro-2-methoxy-2,3-dihydro-1H-inden-1-yl]sulfamide

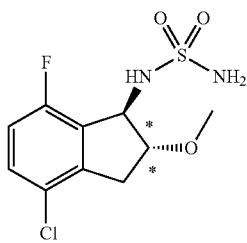 [SMILES: CO[C@@H]1Cc2c(Cl)ccc(F)c2[C@H]1NS(N)(=O)=O]

To the product in Example 18-(4) (321 mg, 1.02 mmol) was added 4N HCl in AcOEt (2 ml) and the mixture was stirred for 10 minutes at room temperature. The solvent was evaporated in vacuo and the residue was dissolved in DCM (5 ml). To the solution were added sulfamoyl chloride (235 mg, 2.03 mmol) and TEA (0.425 mL, 3.05 mmol) at 0° C. and the reaction mixture was stirred for 20 minutes at room temperature. To the reaction mixture were added AcOEt and 2N HCl, and the layers were separated. The organic layer was washed with brine, dried over anhydrous MgSO$_4$ and the solvent was concentrated in vacuo. The residue was purified by silicagel flash column chromatography (Yamazen HI-FLASH™ column Amino, L size, 40 mL/min, gradient 30% to 90% AcOEt in n-heptane) to afford the title compound (187 mg, 0.634 mmol) as a racemate.

Optical resolution of the obtained racemate (187 mg, 0.634 mmol) was conducted by HPLC (CHIRALPAK™ ID, 20 mm I.D.×250 mm, 10% EtOH in n-hexane, 10 mL/min) to afford the title (+)-isomer (50.2 mg, 0.170 mmol, >99% ee), which was eluted second with retention time of 31 min among the 2 optical isomers.

ESI-MS; m/z: 317[M+Na]$^+$ $^1$H-NMR (400 MHz, DMSO-d$_6$)

δ (ppm): 3.06-3.15 (m, 1H), 3.32 (s, 3H), 3.89-3.92 (m, 1H), 4.78 (dd, J=15.8, 8.2 Hz, 1H), 5.25 (dd, J=15.8, 6.0 Hz, 1H), 5.87-5.93 (m, 1H), 6.10-6.14 (m, 1H), 7.37-7.45 (m, 1H), 7.91 (dd, J=7.7, 1.9 Hz, 1H).

Example 19

Synthesis of N-[(1S)-4,7-difluoro-2,3-dihydro-1H-inden-1-yl]sulfamide

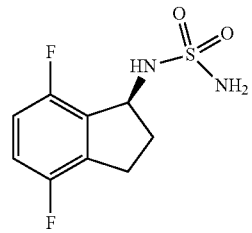 [SMILES: NS(=O)(=O)N[C@H]1CCc2c(F)ccc(F)c21]

(1) Synthesis of t-butyl N-(4,7-difluoro-2,3-dihydro-1H-inden-1-yl)sulfamoylcarbamate

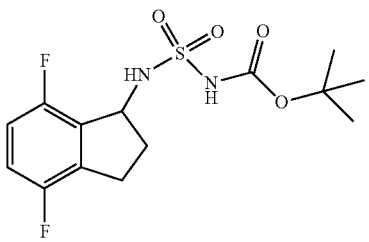 [SMILES: CC(C)(C)OC(=O)NS(=O)(=O)NC1CCc2c(F)ccc(F)c21]

To a solution of 4,7-difluoro-2,3-dihydro-1H-inden-1-amine (CAS No. 625471-13-8, 1.19 g, 11.2 mmol) in DCM (50 mL) were added [(tert-Butoxy)carbonyl]{[4-(dimethyliminio)pyridin-1(4H)-yl]sulfonyl}amide (3.70 g, 12.3 mmol) and TEA (4.66 mL, 33.5 mmol) at room temperature. The resulting solution was stirred for 75 hours at room temperature. The reaction mixture was diluted with AcOEt and 1N HCl and the layers were separated. The organic layer was dried over anhydrous Na$_2$SO$_4$ and evaporated in vacuo to afford the title compound (3.82 g, 11.0 mmol).

ESI-MS; m/z: 371 [M+Na]$^+$ $^1$H-NMR (400 MHz, DMSO-d$_6$)

δ (ppm): 1.44 (s, 9H), 2.02 (ddt, J=13.3, 8.8, 4.6, 1H), 2.36-2.45 (m, 1H), 2.81 (ddd, J=15.4, 8.0, 4.0 Hz, 1H), 3.03

(dt, J=15.4, 7.5 Hz, 1H), 5.00 (td, J=8.0, 4.1 Hz, 1H), 7.00-7.06 (m, 1H), 7.13 (td, J=8.5, 3.7 Hz, 1H), 8.20 (d, J=9.4 Hz, 1H), 10.91 (brs, 1H).

(2) Synthesis of N-[(1S)-4,7-difluoro-2,3-dihydro-1H-inden-1-yl]sulfamide

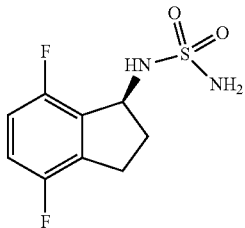 [SMILES: NS(=O)(=O)N[C@H]1CCc2c(F)ccc(F)c21]

To a solution of the product obtained in Example 19-(1) (3.81 g, 11.0 mmol) in MeOH (10 ml) was added 4N HCl in AcOEt (41.1 ml, 165 mmol) and the mixture was stirred at room temperature for 14 hours. The solvent was evaporated in vacuo and the residue was dried to afford the title compound as a mixture. The residue was purified by silicagel column chromatography (AcOEt) to afford the title compound as a racemate (2.24 g, 9.02 mmol).

Optical resolution of the obtained racemate (900 mg, 3.63 mmol) was conducted by HPLC (CHIRALPAK™ IA, 20 mm I.D.×250 mm, 30% EtOH in n-hexane, 10 mL/min) to afford the title (S)-form (380 mg, 1.53 mmol, >99% ee) as white solids, which was eluted second with retention time of 19 min among the 2 optical isomers.

ESI-MS; m/z: 271[M+Na]$^+$ $^1$H-NMR (400 MHz, DMSO-d$_6$)

δ (ppm): 2.17-2.24 (m, 1H), 2.35-2.44 (m, 1H), 2.80 (ddd, J=16.2, 8.7, 4.2 Hz, 1H), 3.05 (dt, J=16.2, 7.8 Hz, 1H), 4.95 (td, J=8.2, 3.5 Hz, 1H), 6.64 (brs, 2H), 7.00-7.14 (m, 3H).

Example 20

Synthesis of (+)-N-(7-chloro-4-fluoro-2,3-dihydro-1H-inden-1-yl)sulfamide

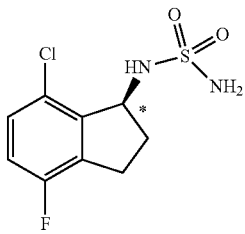 [SMILES: NS(=O)(=O)N[C@H]1CCc2c(F)ccc(Cl)c21]

The title compound (229 mg, 0.87 mmol) was obtained as a racemate from 7-chloro-4-fluoro-2,3-dihydro-1H-inden-1-amine (CAS No. 1337367-67-5, 198 mg, 1.07 mmol) by a similar method as described in Example 19.

ESI-MS; m/z: 287[M+Na]$^+$

Optical resolution of the obtained racemate (190 mg, 0.72 mmol) was conducted by HPLC (CHIRALPAK™ AD-H, 20 mm I.D.×250 mm, 30% EtOH in n-hexane, 10 mL/min) to afford the title compound (+)-form (73 mg, 0.28 mmol. >99% ee) with retention time of 30 min among the 2 optical isomers.

$^1$H-NMR (400 MHz, CDCl$_3$)

δ (ppm): 2.39-2.55 (m, 2H), 2.96-3.03 (m, 1H), 3.10-3.19 (m, 1H), 4.53 (d, J=6.6 Hz, 1H), 4.64 (brs, 2H), 5.06 (td, J=6.6, 2.5 Hz, 1H), 6.97 (t, J=8.8 Hz, 1H), 7.19 (dd, J=8.8, 4.1 Hz, 1H).

Example 21

Synthesis of N-[(1S)-7-chloro-5-fluoro-2,3-dihydro-1H-inden-1-yl]sulfamide

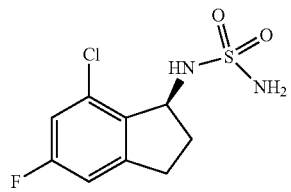 [SMILES: NS(=O)(=O)N[C@H]1CCc2cc(F)cc(Cl)c21]

(1) Synthesis of t-butyl N-(7-chloro-5-fluoro-2,3-dihydro-1H-inden-1-yl)sulfamoylcarbamate

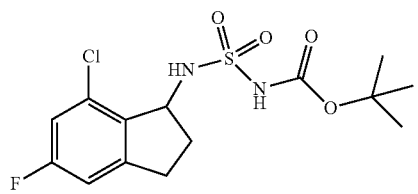 [SMILES: CC(C)(C)OC(=O)NS(=O)(=O)NC1CCc2cc(F)cc(Cl)c21]

The title compound (200 mg, 0.548 mmol) was obtained from 7-chloro-5-fluoro-2,3-dihydro-1H-inden-1-amine (CAS No. 1337210-62-4, 110 mg, 0.593 mmol) by a similar method as described in Example 19-(1).

ESI-MS; m/z: 387[M+Na]$^+$ $^1$H-NMR (400 MHz, CDCl$_3$)

δ (ppm): 1.50 (s, 9H), 2.26-2.52 (m, 2H), 2.88 (ddd, J=16.5, 8.5, 2.1 Hz, 1H), 3.18 (dt, J=16.5, 8.5 Hz, 1H), 5.00 (d, J=6.3 Hz, 1H), 5.17 (brs, 1H), 6.84-6.93 (m, 1H), 6.93-7.05 (m, 1H).

(2) Synthesis of N-[(1S)-7-chloro-5-fluoro-2,3-dihydro-1H-inden-1-yl]sulfamide

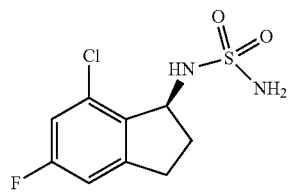 [SMILES: NS(=O)(=O)N[C@H]1CCc2cc(F)cc(Cl)c21]

The title compound (118 mg, 0.446 mmol) was obtained as a racemate from the product obtained in Example 21-(1) by a similar method as described in Example 19-(2). Optical resolution of the obtained racemate (60 mg, 0.227 mmol) was conducted by HPLC (CHIRALCEL™ OJ-H, 20 mm I.D.× 250 mm, 20% EtOH in n-hexane, 10 mL/min) to afford the title compound (26.4 mg, 0.10 mmol. >99% ee), which was eluted second with retention time of 67 min among the 2 optical isomers.

ESI-MS; m/z: 287[M+Na]+

¹H-NMR (400 MHz, CDCl₃)

δ (ppm): 2.29-2.60 (m, 2H), 2.91 (ddd, J=16.6, 8.5, 2.1 Hz, 1H), 3.18 (dt, J=16.6, 8.5 Hz, 1H), 4.47 (d, J=5.7 Hz, 1H), 4.63 (brs, 2H), 4.91-5.12 (m, 1H), 6.86-6.93 (m, 1H), 6.94-7.02 (m, 1H).

Example 22

Synthesis of (+)-N-(7-chloro-5-cyano-2,3-dihydro-1H-inden-1-yl)sulfamide (22a) and (−)-N-(7-chloro-5-cyano-2,3-dihydro-1H-inden-1-yl)sulfamide (22b)

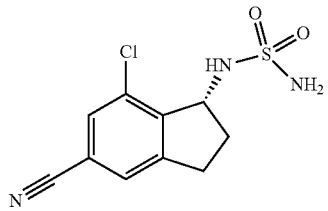

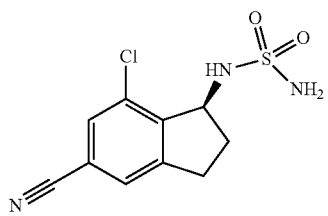

(1) Synthesis of t-butyl N-(7-chloro-5-cyano-2,3-dihydro-1H-inden-1-yl)sulfamoylcarbamate

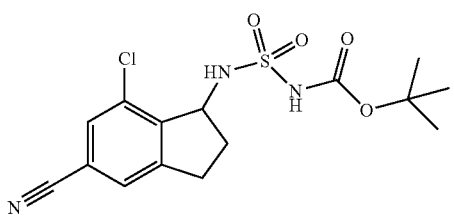 [SMILES: CC(C)(C)OC(=O)NS(=O)(=O)NC1CCc2cc(C#N)cc(Cl)c21]

The title compound (5.45 g, 14.7 mmol) was obtained from 7-chloro-5-cyano-2,3-dihydro-1H-inden-1-amine (CAS No. 1337127-29-3, 3.1 g, 16.1 mmol) by a similar method as described in Example 19-(1).

ESI-MS; m/z: 394[M+Na]+

¹H-NMR (400 MHz, DMSO-d₆)

δ (ppm): 1.42 (s, 9H), 2.03 (ddt, J=13.6, 7.9, 3.0 Hz, 1H), 2.23-2.38 (m, 1H), 2.78-2.90 (m, 1H), 3.12 (dt, J=16.5, 8.4 Hz, 1H), 4.91 (td, J=8.2, 2.6 Hz, 1H), 7.72 (d, J=1.2 Hz, 1H), 7.82 (d, J=1.2 Hz, 1H), 8.13 (d, J=8.2 Hz, 1H), 10.96 (s, 1H).

(2) Synthesis of (+)-N-(7-chloro-5-cyano-2,3-dihydro-1H-inden-1-yl)sulfamide (22a) and (−)-N-(7-chloro-5-cyano-2,3-dihydro-1H-inden-1-yl)sulfamide (22b)

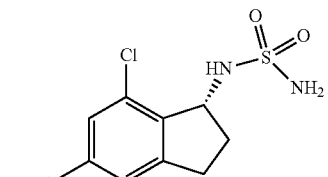

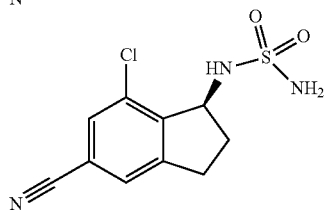

The title compound (3.50 g, 12.9 mmol) was obtained as a racemate from the product obtained in Example 22-(1) (5.40 g, 14.5 mmol) by a similar method as described in Example 19-(2).

Optical resolution of the obtained racemate (570 mg, 2.01 mmol) was conducted by HPLC (CHIRALPAK™ IC, 20 mm I.D.×250 mm, 30% EtOH in n-hexane, 10 mL/min) to afford the (+)-form of the title compound (252 mg, 0.927 mmol. >99% ee) with retention time of 26 min and the (−)-form of the title compound (251 mg, 0.924 mmol. >99% ee) with retention time of 34 min.

The property values of the (+)-form are as follows.

ESI-MS; m/z: 294[M+Na]+

¹H-NMR (400 MHz, CDCl₃)

δ (ppm): 2.19-2.34 (m, 2H), 2.77-2.91 (m, 1H), 3.15 (dt, J=16.5, 8.5 Hz, 1H), 4.86 (ddd, J=9.1, 6.0, 3.6 Hz, 1H), 6.66 (s, 2H), 7.00 (d, J=9.1 Hz, 1H), 7.71 (d, J=1.2 Hz, 1H), 7.80 (d, J=1.2 Hz, 1H).

The property values of the (−)-form are as follows.

ESI-MS; m/z: 294[M+Na]+

¹H-NMR (400 MHz, CDCl₃)

δ (ppm): 2.19-2.34 (m, 2H), 2.77-2.91 (m, 1H), 3.15 (dt, J=16.5, 8.5 Hz, 1H), 4.86 (ddd, J=9.1, 6.0, 3.6 Hz, 1H), 6.66 (s, 2H), 7.00 (d, J=9.1 Hz, 1H), 7.71 (d, J=1.2 Hz, 1H), 7.80 (d, J=1.2 Hz, 1H).

Example 23

Synthesis of (−)-N-(5-chloro-7-fluoro-2,3-dihydro-1H-inden-1-yl)sulfamide

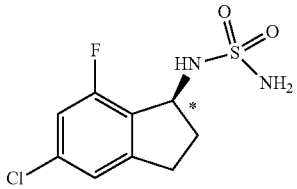 [SMILES: NS(=O)(=O)N[C@H]1CCc2cc(Cl)cc(F)c21]

(1) Synthesis of t-butyl N-(5-chloro-7-fluoro-2,3-dihydro-1H-inden-1-yl)sulfamoylcarbamate

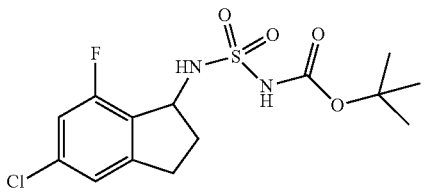 [SMILES: CC(C)(C)OC(=O)NS(=O)(=O)NC1CCc2cc(Cl)cc(F)c21]

The title compound (176 mg, 0.482 mmol) was obtained from 5-chloro-7-fluoro-2,3-dihydro-1H-inden-1-amine (CAS No. 1337693-39-6, 96 mg, 0.517 mmol) by a similar method as described in Example 19-(1).

ESI-MS; m/z: 387[M+Na]$^+$ $^1$H-NMR (400 MHz, CDCl$_3$)

δ (ppm): 1.49 (s, 9H), 2.26-2.37 (m, 1H), 2.40-2.53 (m, 1H), 2.86 (ddd, J=16.5, 8.6, 3.9 Hz, 1H), 3.12 (dt, J=16.5, 8.6 Hz, 1H), 5.05 (td, J=6.8, 3.2 Hz, 1H), 5.31 (d, J=6.8 Hz, 1H), 6.88-6.97 (m, 1H), 7.07 (s, 1H), 7.15 (brs, 1H).

(2) Synthesis of (−)-N-(5-chloro-7-fluoro-2,3-dihydro-1H-inden-1-yl)sulfamide

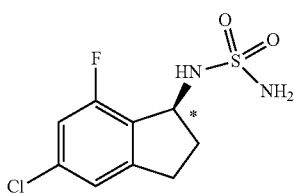 [SMILES: NS(=O)(=O)N[C@H]1CCc2cc(Cl)cc(F)c21]

The title compound (114 mg, 0.431 mmol) was obtained as a racemate from the product obtained in Example 23-(1) (176 mg, 0.482 mmol) by a similar method as described in Example 19-(2).

Optical resolution of the obtained racemate (110 mg, 0.416 mmol) was conducted by HPLC (CHIRALPAK™ IE, 20 mm I.D.×250 mm, 20% EtOH in n-hexane, 10 mL/min) to afford the (−)-form of the title compound (46 mg, 0.174 mmol. >99% ee), which was eluted second with retention time of 28 min among the 2 optical isomers.

ESI-MS; m/z: 287[M+Na]$^+$ $^1$H-NMR (400 MHz, CDCl$_3$)

δ (ppm): 2.18-2.39 (m, 1H), 2.46-2.65 (m, 1H), 2.87 (ddd, J=16.6, 8.6, 5.3 Hz, 1H), 3.00-3.18 (m, 1H), 4.64 (brs, 3H), 5.12 (td, J=7.5, 4.3 Hz, 1H), 6.90-6.99 (m, 1H), 7.07 (d, J=1.0 Hz, 1H).

Example 24

Synthesis of (+)-N-(7-chloro-2,3-dihydro-1H-inden-1-yl)sulfamide

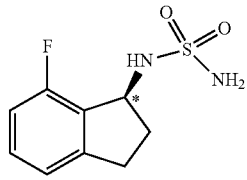 [SMILES: NS(=O)(=O)N[C@H]1CCc2cccc(F)c21]

(1) Synthesis of t-butyl N-(7-chloro-2,3-dihydro-1H-inden-1-yl)sulfamoylcarbamate

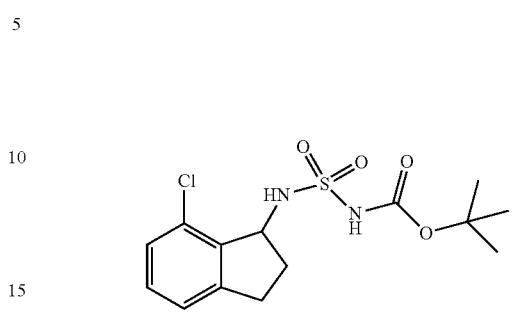

The title compound (213 mg, 0.614 mmol) was obtained from 7-chloro-2,3-dihydro-1H-inden-1-amine (CAS No. 67120-37-0, 203 mg, 1.21 mmol) by a similar method as described in Example 19-(1).

ESI-MS; m/z: 369[M+Na]$^+$ $^1$H-NMR (400 MHz, CDCl$_3$)

δ (ppm): 1.50 (s, 9H), 2.26-2.38 (m, 1H), 2.38-2.47 (m, 1H), 2.89 (ddd, J=16.4, 8.5, 2.4 Hz, 1H), 3.13-3.25 (m, 1H), 5.01-5.07 (m, 1H), 5.16 (d, J=5.5 Hz, 1H), 7.15-7.25 (m, 4H).

(2) Synthesis of (+)-N-(7-chloro-2,3-dihydro-1H-inden-1-yl)sulfamide

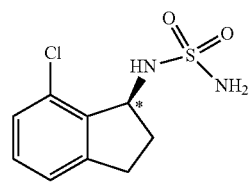 [SMILES: NS(=O)(=O)N[C@H]1CCc2cccc(Cl)c21]

The title compound (108 mg, 0.438 mmol) was obtained as a racemate from the product obtained in Example 24-(1) (213 mg, 0.614 mmol) by a similar method as described in Example 19-(2).

Optical resolution of the obtained racemate (30 mg, 0.122 mmol) was conducted by HPLC (CHIRALPAK™ IC, 20 mm I.D.×250 mm, 20% EtOH in n-hexane, 10 mL/min) to afford the (+)-form of the title compound (12.1 mg, 0.049 mmol. >99% ee), which was eluted second with retention time of 34 min among the 2 optical isomers.

ESI-MS; m/z: 269 [M+Na]$^+$ $^1$H-NMR (400 MHz, CDCl$_3$)

δ (ppm): 2.31-2.55 (m, 2H), 2.86-2.98 (m, 1H), 3.19 (dt, J=16.6, 8.5 Hz, 1H), 4.50 (d, J=5.5 Hz, 1H), 4.63 (brs, 2H), 5.06 (td, J=6.6, 2.2 Hz, 1H), 7.16-7.26 (m, 3H).

Example 25

Synthesis of (+)-N-(5-cyano-7-methyl-2,3-dihydro-1H-inden-1-yl)sulfamide (25a) and (−)-N-(5-cyano-7-methyl-2,3-dihydro-1H-inden-1-yl)sulfamide (25b)

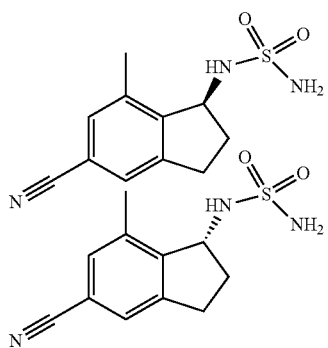

The title compound (220 mg, 0.875 mmol) was obtained as a racemate from 5-cyano-7-methyl-2,3-dihydro-1H-inden-1-amine (CAS No. 1337245-99-4, 0.50 g, 2.90 mmol) by a similar method as described in Example 19. Optical resolution of the obtained racemate (109 mg, 0.432 mmol) was conducted by HPLC (CHIRALPAK™ IF, 20 mm I.D.×250 mm, 20% EtOH in n-hexane, 10 mL/min). The obtained isomers were analyzed by CHIRALPAK™ IF (4.6 mm I.D.× 150 mm, 20% EtOH in n-hexane, 1 mL/min). The (+)-form (46 mg, 0.182 mmol, >99% ee) with a retention time of 8 min and the (−)-form (44 mg, 0.177 mmol, >99% ee) with a retention time of 9 min were obtained.

The property values of the (+)-form are as follows.
ESI-MS; m/z: 274 [M+Na]$^+$
$^1$H-NMR (400 MHz, DMSO-d$_6$)
δ (ppm): 2.14-2.35 (m, 2H), 2.37 (s, 3H), 2.76 (ddd, J=16.1, 8.3, 3.3 Hz, 1H), 3.09 (ddd, J=16.1, 8.3, 8.3 Hz, 1H), 4.77-4.85 (m, 1H), 6.71 (brs, 2H), 6.94 (d, J=9.0 Hz, 1H), 7.45 (s, 1H), 7.53 (s, 1H).

The property values of the (−)-form are as follows.
ESI-MS; m/z: 274 [M+Na]$^+$
$^1$H-NMR (400 MHz, DMSO-d$_6$)
δ (ppm): 2.14-2.35 (m, 2H), 2.37 (s, 3H), 2.76 (ddd, J=16.1, 8.3, 3.3 Hz, 1H), 3.09 (ddd, J=16.1, 8.3, 8.3 Hz, 1H), 4.77-4.85 (m, 1H), 6.71 (brs, 2H), 6.94 (d, J=9.0 Hz, 1H), 7.45 (s, 1H), 7.53 (s, 1H).

Example 26

Synthesis of (±)-N-(5-fluoro-7-methyl-2,3-dihydro-1H-inden-1-yl)sulfamide

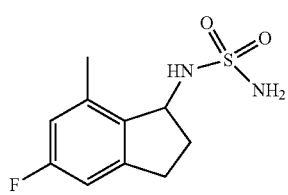 [SMILES: Cc1cc(F)cc2c1C(NS(N)(=O)=O)CC2]

(1) Synthesis of t-butyl N-(5-fluoro-7-methyl-2,3-dihydro-1H-inden-1-yl)sulfamoylcarbamate

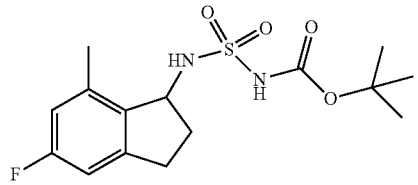 [SMILES: Cc1cc(F)cc2c1C(NS(=O)(=O)NC(=O)OC(C)(C)C)CC2]

The title compound (187 mg, 0.543 mmol) was obtained from 5-fluoro-7-methyl-2,3-dihydro-1H-inden-1-amine (CAS No. 1337122-58-3, 95 mg, 0.575 mmol) by a similar method as described in Example 19-(1).
ESI-MS; m/z: 367 [M+Na]$^+$
$^1$H-NMR (400 MHz, CDCl$_3$)
δ (ppm): 1.51 (s, 9H), 2.19-2.47 (m, 5H), 2.82 (ddd, J=16.6, 8.3, 3.2 Hz, 1H), 3.07 (dt, J=16.6, 8.3 Hz, 1H), 4.87-5.10 (m, 2H), 6.67-6.85 (m, 2H), 7.19 (brs, 1H).

(2) Synthesis of (±)-N-(5-fluoro-7-methyl-2,3-dihydro-1H-inden-1-yl)sulfamide

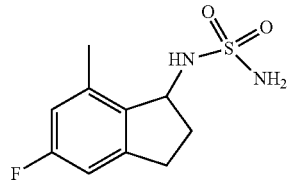 [SMILES: Cc1cc(F)cc2c1C(NS(N)(=O)=O)CC2]

The title compound (9 mg, 0.037 mmol) was obtained as a racemate from the product obtained in Example 26-(1) (185 mg, 0.537 mmol) by a similar method as described in Example 19-(2).
ESI-MS; m/z: 267 [M+Na]$^+$
$^1$H-NMR (400 MHz, CDCl$_3$)
δ (ppm): 2.32-2.47 (m, 5H), 2.75-2.90 (m, 1H), 3.08 (dt, J=16.7, 8.4 Hz, 1H), 4.30 (d, J=8.2 Hz, 1H) 4.61 (brs, 2H), 4.89-5.04 (m, 1H), 6.68-6.82 (m, 2H).

Example 27

Synthesis of (+)-N-(7-methyl-2,3-dihydro-1H-inden-1-yl)sulfamide

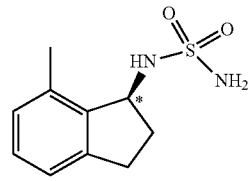

The title compound (224 mg, 1.91 mmol) was obtained as a racemate from 7-methyl-2,3-dihydro-1H-inden-1-amine (CAS No. 168902-78-1, 437 mg, 2.97 mmol) by a similar method as described in Example 19.

$^1$H-NMR (400 MHz, CDCl$_3$)

δ (ppm): 2.33-2.45 (m, 5H), 2.81-2.91 (m, 1H), 3.04-3.16 (m, 1H), 4.29 (d, J=7.4 Hz, 1H), 4.56 (brs, 2H), 4.99-5.08 (m, 1H), 7.03 (d, J=7.4 Hz, 1H), 7.10 (d, J=7.4 Hz, 1H), 7.20 (t, J=7.4, 1H).

Optical resolution of the obtained racemate (174 mg, 0.769 mmol) was conducted by HPLC (CHIRALPAK™ IE, 20 mm I.D.×250 mm, 15% EtOH in n-hexane, 10 mL/min) to afford the (+)-form (67 mg, 0.295 mmol, >99% ee), which was eluted first among the 2 optical isomers.

As a result of analysis of the isomer by CHIRALPAK™ IE (4.6 mm I.D.×150 mm, 15% EtOH in n-hexane, 1 mL/min), the (+)-form had a retention time of 6 min and the property value of the (+)-form is as follows.

ESI-MS; m/z: 249 [M+Na]$^+$

Example 28

Synthesis of (+)-N-(4-fluoro-7-methyl-2,3-dihydro-1H-inden-1-yl)sulfamide (28a) and (−)-N-(4-fluoro-7-methyl-2,3-dihydro-1H-inden-1-yl)sulfamide (28b)

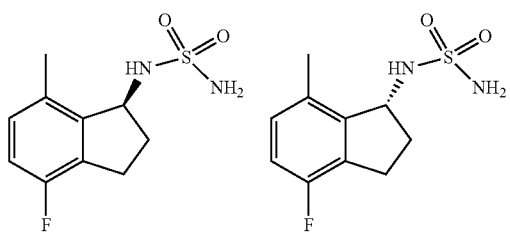 [SMILES: Cc1ccc(F)c2c1[C@@H](NS(N)(=O)=O)CC2 ; Cc1ccc(F)c2c1[C@H](NS(N)(=O)=O)CC2]

(1) Synthesis of benzyl N-(4-fluoro-7-methyl-2,3-dihydro-1H-inden-1-yl)sulfamoylcarbamate

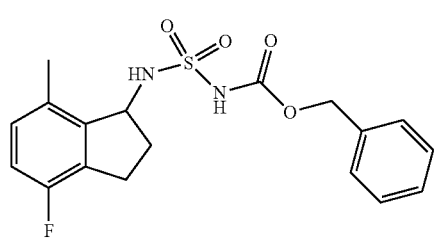 [SMILES: Cc1ccc(F)c2c1C(NS(=O)(=O)NC(=O)OCc1ccccc1)CC2]

The title compound (248 mg, 0.655 mmol) was obtained from 4-fluoro-7-methyl-2,3-dihydro-1H-inden-1-amine (CAS No. 1337048-34-6, 117 mg, 0.708 mmol) by a similar method as described in Example 1-(4).

ESI-MS; m/z: 401 [M+Na]$^+$ $^1$H-NMR (400 MHz, CDCl$_3$)

δ (ppm): 2.05-2.16 (m, 1H), 2.19-2.32 (m, 4H), 2.83 (ddd, J=16.7, 8.7, 3.3 Hz, 1H), 2.87-2.98 (m, 1H), 4.94-5.03 (m, 1H), 5.09-5.15 (m, 1H), 5.17-5.25 (m, 2H), 6.87 (t, J=8.4 Hz, 1H), 6.93-7.00 (m, 1H), 7.35-7.40 (m, 5H).

(2) Synthesis of (+)-N-(4-fluoro-7-methyl-2,3-dihydro-1H-inden-1-yl)sulfamide (28a) and (−)-N-(4-fluoro-7-methyl-2,3-dihydro-1H-inden-1-yl)sulfamide (28b)

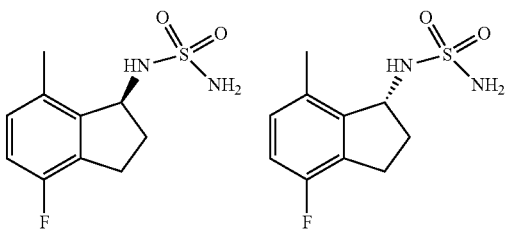 [SMILES: Cc1ccc(F)c2c1[C@@H](NS(N)(=O)=O)CC2 ; Cc1ccc(F)c2c1[C@H](NS(N)(=O)=O)CC2]

The title compound (144 mg, 0.589 mmol) was obtained as a racemate from the product obtained in Example 28-(1) (245 mg, 0.647 mmol) by a similar method as described in Example 1-(5).

Optical resolution of the obtained racemate (130 mg, 0.532 mmol) was conducted by HPLC (CHIRALPAK™ IA, 20 mm I.D.×250 mm, 15% EtOH in n-hexane, 10 mL/min) to afford the (−)-form (28b) (57 mg, 0.233 mmol, >99% ee) with retention time of 21 min and the (+)-form (28a) (53 mg, 0.217 mmol, >99% ee) with retention time of 25 min.

The property values of the (−)-form are as follows.

ESI-MS; m/z: 267 [M+Na]$^+$ $^1$H-NMR (400 MHz, CDCl$_3$)

δ (ppm): 2.32-2.48 (m, 5H), 2.94 (dt, J=16.7, 5.9 Hz, 1H), 3.06 (dt, J=16.7, 8.3 Hz, 1H), 4.34 (d, J=7.4 Hz, 1H), 4.62 (brs, 2H), 4.95-5.08 (m, 1H), 6.89 (t, J=8.5 Hz, 1H), 6.99 (dd, J=8.5, 4.9 Hz, 1H).

The property values of the (+)-form are as follows.

ESI-MS; m/z: 267 [M+Na]$^+$ $^1$H-NMR (400 MHz, CDCl$_3$)

δ (ppm): 2.32-2.48 (m, 5H), 2.94 (dt, J=16.7, 5.9 Hz, 1H), 3.06 (dt, J=16.7, 8.3 Hz, 1H), 4.34 (d, J=7.4 Hz, 1H), 4.62 (brs, 2H), 4.95-5.08 (m, 1H), 6.89 (t, J=8.5 Hz, 1H), 6.99 (dd, J=8.5, 4.9 Hz, 1H).

Example 29

Synthesis of (−)-N-(4,6,7-trifluoro-2,3-dihydro-1H-inden-1-yl)sulfamide

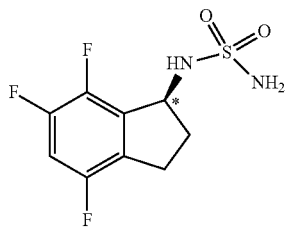 [SMILES: NS(=O)(=O)N[C@H]1CCc2c(F)cc(F)c(F)c21]

The title compound (370 mg, 1.39 mmol) was obtained as a racemate from 4,6,7-trifluoro-2,3-dihydro-1H-inden-1-amine (CAS No. 1337125-68-4, 1.10 g, 5.90 mmol) by a similar method as described in Example 1-(4) and 1-(5).

Optical resolution of the obtained racemate (340 mg, 1.28 mmol) was conducted by HPLC (CHIRALPAK™ IC, 20 mm I.D.×250 mm, 20% EtOH in n-hexane, 10 mL/min) to afford the title compound (−)-form (157 mg, 0.590 mmol. >99% ee), that was eluted first with retention time of 18 min among the 2 optical isomers.

ESI-MS; m/z: 289 [M+Na]$^+$
$^1$H-NMR (400 MHz, CDCl$_3$)
δ (ppm): 2.20-2.39 (m, 1H), 2.53-2.76 (m, 1H), 2.80-2.97 (m, 1H), 2.98-3.16 (m, 1H), 4.54-4.83 (m, 3H), 5.13-5.29 (m, 1H), 6.87 (ddd, J=10.0, 7.8, 5.9 Hz, 1H).

Example 30

Synthesis of (±)-N-(5-chloro-7-methyl-2,3-dihydro-1H-inden-1-yl)sulfamide

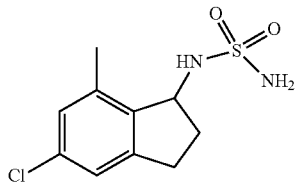 [SMILES: Cc1cc(Cl)cc2c1C(NS(N)(=O)=O)CC2]

Benzyl N-(5-chloro-7-methyl-2,3-dihydro-1H-inden-1-yl)sulfamoylcarbamate (196 mg, 0.497 mmol) was obtained from 5-chloro-7-methyl-2,3-dihydro-1H-inden-1-amine (CAS No. 1337697-66-1, 121 mg, 0.666 mmol) by a similar method as described in Example 1-(4).

The title compound (71 mg, 0.272 mmol) was obtained as a racemate from benzyl N-(5-chloro-7-methyl-2,3-dihydro-1H-inden-1-yl)sulfamoylcarbamate (168 mg, 0.425 mmol) by a similar method as described in Example 1-(5).

ESI-MS; m/z: 283 [M+Na]$^+$
$^1$H-NMR (400 MHz, CDCl$_3$)
δ (ppm): 2.34-2.46 (m, 5H), 2.84 (ddd, J=16.5, 7.3, 4.3 Hz, 1H), 3.08 (ddd, J=16.5, 8.4, 8.4, 1H), 4.25 (d, J=7.8 Hz, 1H), 4.56 (brs, 2H), 4.94-5.04 (m, 1H), 7.03 (s, 1H), 7.08 (s, 1H).

Example 31

Synthesis of (−)-N-(4-chloro-7-fluoro-2,3-dihydro-1H-inden-1-yl)sulfamide

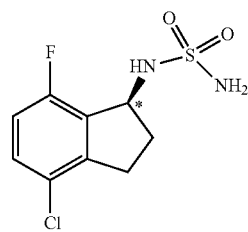 [SMILES: NS(=O)(=O)N[C@H]1CCc2c(Cl)ccc(F)c21]

To a solution of 4-chloro-7-fluoro-2,3-dihydro-1H-inden-1-amine (CAS No. 1337690-24-0, 371 mg, 2.00 mmol) and TEA (0.697 mL, 5.00 mmol) in DCM (10 mL) was added sulfamoyl chloride (462 mg, 4.00 mmol) at 0° C. The reaction mixture was stirred for 3 hours at room temperature. To the reaction mixture were added AcOEt and water, and the layers were separated. The organic layer was washed with brine, dried over anhydrous Na$_2$SO$_4$. The solvent was concentrated in vacuo and the residue was purified by silicagel column chromatography (gradient 20% to 33% AcOEt in n-heptane) to afford the title compound (165 mg, 0.623 mmol) as a racemate.

Optical resolution of the obtained racemate (139 mg, 0.525 mmol) was conducted by HPLC (CHIRALPAK™ IA, 20 mm I.D.×250 mm, 25% EtOH in n-hexane, 10 mL/min) to afford the title compound (−)-form (52 mg, 0.196 mmol. >99% ee), that was eluted second with retention time of 22 min among the 2 optical isomers.

ESI-MS; m/z: 287, 289 [M+Na]$^+$
$^1$H-NMR (400 MHz, CDCl$_3$)
δ (ppm): 2.26-2.34 (m, 1H), 2.57-2.66 (m, 1H), 2.88-2.96 (m, 1H), 3.08-3.16 (m, 1H), 4.63 (brs, 2H), 4.66 (brs, 1H), 5.19-5.24 (m, 1H), 6.90 (t, J=8.8 Hz, 1H), 7.24-7.27 (m, 1H).

Reference Example 1

X-ray crystallographic analysis of N-[(1S)-2,2,5,7-tetrafluoro-2,3-dihydro-1H-inden-1-yl]sulfamide The white solids obtained in Example 1-(5) were dissolved in MeOH and toluene and recrystallized by solvent evaporation method. X-ray diffraction analysis was conducted using the obtained single crystal. The results of data collection and crystallographic analysis are summarized in Table 1, and the atomic coordinates are shown in Tables 2. The absolute configuration of the title compound was specified from such results.

TABLE 1

| | |
|---|---|
| Temperature | 100 K |
| Wavelength | 0.7107 Å |
| Crystal system, space group | Monoclinic, I2 |
| Lattice parameters | a = 12.975 (7) Å |
| | b = 4.963 (3) Å |
| | c = 33.74 (2) Å |
| | β = 98.15 (2)° |
| Volume | 2151 (2) Å$^3$ |
| Z value, calculated density | 8, 1.755 g/cm$^3$ |
| Crystal dimentions | 0.20 × 0.10 × 0.10 mm |
| Total number of reflections/ number of unique reflections | 7908/4056 [R$_{int}$ = 0.0412] |
| Completeness | 70.1% |
| Structure solution | Direct methods (SHELX97) |
| Refinement | Full-matrix least-squares on F$^2$ |
| Reflection/parameter | 4056/341 |
| Goodness of fit indicator | 1.066 |
| R factor (all data) | 0.0398 |
| R factor (I > 2σ (I)) | 0.0389 |
| Flack parameter | −0.12 (8) |
| The maximum and minimum peaks on the final difference Fourier map | 0.52 and −0.47 e/Å$^3$ |

TABLE 2

| Atom | x | y | z | B (eq) |
|---|---|---|---|---|
| S1 | 0.66860(5) | 1.1453(2) | 0.04848(2) | 0.523(13) |
| S2 | 0.33982(5) | −0.3815(2) | 0.08182(2) | 0.534(13) |
| F1 | 0.9462(2) | 1.1782(6) | 0.03401(6) | 2.55(5) |
| F2 | 0.8837(2) | 0.7746(5) | 0.02197(5) | 1.94(4) |
| F3 | 1.0477(2) | 0.1913(5) | 0.18786(5) | 1.72(4) |
| F4 | 0.76903(13) | 0.7856(5) | 0.15680(5) | 1.45(4) |
| F5 | 0.2629(2) | −0.4533(5) | 0.18975(6) | 1.63(4) |
| F6 | 0.22095(13) | −0.0561(5) | 0.16562(6) | 1.79(4) |
| F7 | 0.6409(2) | 0.5667(5) | 0.24296(7) | 3.28(6) |
| F8 | 0.5767(2) | 0.0236(5) | 0.12874(6) | 1.73(4) |
| O1 | 0.6856(2) | 1.3908(5) | 0.07134(6) | 0.87(4) |
| O2 | 0.5685(2) | 1.0201(5) | 0.04407(6) | 0.83(4) |

TABLE 2-continued

| Atom | x | y | z | B (eq) |
|------|---|---|---|--------|
| O3 | 0.2877(2) | −0.6171(5) | 0.09423(6) | 1.04(4) |
| O4 | 0.2906(2) | −0.2444(5) | 0.04672(6) | 1.01(4) |
| N1 | 0.7474(2) | 0.9234(6) | 0.06963(7) | 0.63(4) |
| N2 | 0.6931(3) | 1.2225(7) | 0.00419(8) | 1.42(6) |
| N3 | 0.3529(2) | −0.1541(6) | 0.11579(7) | 0.89(5) |
| N4 | 0.4581(2) | −0.4747(7) | 0.08027(8) | 1.04(5) |
| C1 | 0.8556(2) | 0.9751(7) | 0.08358(8) | 0.71(5) |
| C2 | 0.9295(3) | 0.9382(8) | 0.05181(9) | 1.30(6) |
| C3 | 1.0297(3) | 0.8054(8) | 0.07165(9) | 1.22(6) |
| C4 | 0.9960(2) | 0.6698(7) | 0.10748(8) | 0.79(5) |
| C5 | 1.0477(2) | 0.4717(7) | 0.13193(9) | 0.93(6) |
| C6 | 1.0004(3) | 0.3878(7) | 0.16354(9) | 1.02(6) |
| C7 | 0.9074(3) | 0.4818(8) | 0.17276(9) | 1.16(6) |
| C8 | 0.8589(2) | 0.6795(8) | 0.14792(9) | 1.09(6) |
| C9 | 0.9001(2) | 0.7762(7) | 0.11510(9) | 0.71(5) |
| C10 | 0.3896(2) | −0.2109(7) | 0.15757(8) | 0.59(5) |
| C11 | 0.3017(3) | −0.2051(7) | 0.18443(9) | 0.95(5) |
| C12 | 0.3446(3) | −0.0697(8) | 0.22358(10) | 1.41(6) |
| C13 | 0.4388(3) | 0.0810(7) | 0.21379(9) | 0.82(5) |
| C14 | 0.4979(3) | 0.2722(8) | 0.23671(9) | 1.49(6) |
| C15 | 0.5824(3) | 0.3787(8) | 0.22139(11) | 1.97(7) |
| C16 | 0.6111(3) | 0.3013(8) | 0.18533(11) | 1.76(7) |
| C17 | 0.5503(3) | 0.1041(7) | 0.16364(9) | 1.03(6) |
| C18 | 0.4642(2) | −0.0010(7) | 0.17711(8) | 0.82(5) |
| H1 | 0.8635 | 1.1616 | 0.0948 | 0.85 |
| H2A | 1.0846 | 0.9410 | 0.0798 | 1.47 |
| H3B | 1.0558 | 0.6726 | 0.0536 | 1.47 |
| H4 | 1.1123 | 0.3988 | 0.1269 | 1.11 |
| H5 | 0.8778 | 0.4147 | 0.1950 | 1.39 |
| H6 | 0.7232 | 0.7605 | 0.0729 | 0.75 |
| H7 | 0.7480 | 1.3235 | 0.0061 | 1.17 |
| H8 | 0.6988 | 1.0969 | −0.0114 | 1.91 |
| H9 | 0.4243 | −0.3912 | 0.1598 | 0.71 |
| H10A | 0.3645 | −0.2047 | 0.2449 | 1.69 |
| H11B | 0.2929 | 0.0555 | 0.2324 | 1.69 |
| H12 | 0.4811 | 0.3279 | 0.2620 | 1.78 |
| H13 | 0.6696 | 0.3786 | 0.1756 | 2.11 |
| H14 | 0.3371 | 0.0132 | 0.1088 | 1.07 |
| H15 | 0.4673 | −0.6088 | 0.0648 | 2.80 |
| H16 | 0.4954 | −0.3328 | 0.0723 | 2.37 |

Reference Example 2

X-ray crystallographic analysis of N-[(1S)-2,2-difluoro-7-methyl-2,3-dihydro-1H-inden-1-yl]sulfamide The white solids obtained in Example 11-(6) were dissolved in EtOH and n-hexane and recrystallized by temperature gradient to afford microcrystals. The microcrystals were dissolved in Et$_2$O and further recrystallized by solvent evaporation method.

X-ray diffraction analysis was conducted using the obtained single crystal. The results of data collection and crystallographic analysis are summarized in Table 3, and the atomic coordinates are shown in Tables 4. The absolute configuration of the title compound was specified from such results.

TABLE 3

| Temperature | 100 K |
|---|---|
| Wavelength | 1.5418 Å |
| Crystal system, space group | Monoclinic, P2$_1$ |
| Lattice parameters | a = 8.6474 (3) Å |
| | b = 7.6050 (2) Å |
| | c = 8.7054 (3) Å |
| | β = 100.345 (3)° |
| Volume | 563.19 (4) Å$^3$ |
| Z value, calculated density | 2, 1.546 g/cm$^3$ |
| Crystal dimentions | 0.20 × 0.10 × 0.10 mm |
| Total number of reflections/ number of unique reflections | 5898/1998 [R$_{int}$ = 0.0479] |
| Completeness | 98.7% |
| Structure solution | Direct methods (SHELX97) |
| Refinement | Full-matrix least-squares on F$^2$ |
| Reflection/parameter | 1998/163 |
| Goodness of fit indicator | 1.128 |
| R factor (all data) | 0.0530 |
| R factor (I > 2σ (I)) | 0.0481 |
| Flack parameter | 0.02 (4) |
| The maximum and minimum peaks on the final difference Fourier map | 0.34 and −1.02 e/Å$^3$ |

TABLE 4

| Atom | x | y | z | B (eq) |
|------|---|---|---|--------|
| S1 | 0.1572(1) | 0.4621(1) | 0.5199(1) | 1.79(3) |
| F2 | 0.0744(3) | 0.5656(4) | 0.8851(3) | 2.63(6) |
| F3 | 0.0241(3) | 0.2859(4) | 0.8642(3) | 2.62(6) |
| O5 | 0.1999(4) | 0.2897(4) | 0.4775(4) | 2.20(6) |
| O18 | 0.1789(4) | 0.6092(4) | 0.4240(4) | 2.46(6) |
| N6 | 0.2664(4) | 0.5054(4) | 0.6876(4) | 1.61(6) |
| N7 | −0.0242(5) | 0.4536(7) | 0.5286(4) | 2.14(7) |
| C8 | 0.1416(6) | 0.4043(6) | 0.9110(5) | 1.97(8) |
| C9 | 0.2761(5) | 0.3829(5) | 0.8175(5) | 1.47(7) |
| C10 | 0.4217(5) | 0.4048(6) | 0.9402(5) | 1.66(7) |
| C11 | 0.5787(5) | 0.4130(6) | 0.9159(5) | 2.10(8) |
| C12 | 0.6927(6) | 0.4239(6) | 1.0487(6) | 2.58(9) |
| C13 | 0.6581(6) | 0.4274(6) | 1.1999(6) | 2.64(9) |
| C14 | 0.5028(6) | 0.4174(6) | 1.2212(5) | 2.44(9) |
| C15 | 0.3858(6) | 0.4041(6) | 1.0885(5) | 1.98(8) |
| C16 | 0.2115(5) | 0.3830(7) | 1.0839(5) | 2.29(9) |
| C17 | 0.6204(6) | 0.4078(8) | 0.7548(6) | 3.0(1) |
| H4 | −0.067(5) | 0.377(7) | 0.559(5) | 0.0(8) |
| H6 | 0.3203 | 0.6041 | 0.7001 | 1.93 |
| H9 | 0.2736 | 0.2601 | 0.7759 | 1.76 |
| H12 | 0.7997 | 0.4293 | 1.0370 | 3.10 |
| H13 | 0.7406 | 0.4365 | 1.2877 | 3.16 |
| H14 | 0.4771 | 0.4196 | 1.3228 | 2.93 |
| H16A | 0.1713 | 0.4745 | 1.1475 | 2.75 |
| H16B | 0.1871 | 0.2656 | 1.1225 | 2.75 |
| H17A | 0.7336 | 0.3880 | 0.7636 | 3.64 |
| H17B | 0.5920 | 0.5200 | 0.7018 | 3.64 |
| H17C | 0.5626 | 0.3122 | 0.6945 | 3.64 |
| H19 | −0.070(8) | 0.55(1) | 0.551(9) | 4(2) |

Reference Example 3

X-ray crystallographic analysis of N-[(1S)-2,2,5-trifluoro-7-methyl-2,3-dihydro-1H-inden-1-yl]sulfamide The white solids obtained in Example 12-(9) were dissolved in EtOH and recrystallized by vapor diffusion method using toluene as reservoir solution.

X-ray diffraction analysis was conducted using the single crystal obtained as above.

The results of data collection and crystallographic analysis are summarized in Table 5, and the atomic coordinates are shown in Tables 6. The absolute configuration of the title compound was specified from such results.

TABLE 5

| Temperature | 100 K |
|---|---|
| Wavelength | 0.7107 Å |
| Crystal system, space group | Monoclinic, P2$_1$ |
| Lattice parameters | a = 4.708 (7) Å |
| | b = 7.495 (11) Å |
| | c = 15.66 (3) Å |
| | β = 90.926 (3)° |

TABLE 5-continued

| | |
|---|---|
| Volume | 553 (2) Å$^3$ |
| Z value, calculated density | 2, 1.684 g/cm$^3$ |
| Crystal dimentions | 0.20 × 0.20 × 0.02 mm |
| Total number of reflections/ number of unique reflections | 6974/2195 [R$_{int}$ = 0.1065] |
| Completeness | 77.4% |
| Structure solution | Direct methods (SHELX97) |
| Refinement | Full-matrix least-squares on F$^2$ |
| Reflection/parameter | 2195/172 |
| Goodness of fit indicator | 1.132 |
| R factor (all data) | 0.0914 |
| R factor (I > 2σ (I)) | 0.0692 |
| Flack parameter | 0.0 (3) |
| The maximum and minimum peaks on the final difference Fourier map | 0.71 and −0.71 e/Å$^3$ |

TABLE 6

| Atom | x | y | z | B (eq) |
|---|---|---|---|---|
| S1 | 1.2336(3) | 0.2417(3) | 0.09702(9) | 1.89(3) |
| F1 | 1.0091(8) | 0.0964(5) | 0.2896(3) | 2.14(7) |
| F2 | 1.4190(8) | 0.1968(6) | 0.3304(3) | 2.33(8) |
| F3 | 0.3417(8) | 0.8204(6) | 0.4194(3) | 2.60(8) |
| O1 | 1.0577(10) | 0.1451(7) | 0.0386(3) | 2.31(9) |
| O2 | 1.4639(10) | 0.1479(7) | 0.1365(3) | 2.21(9) |
| N1 | 1.0183(11) | 0.3243(8) | 0.1649(3) | 1.79(10) |
| N2 | 1.3717(12) | 0.4204(9) | 0.0564(4) | 2.24(11) |
| C1 | 1.1199(13) | 0.3943(9) | 0.2475(4) | 1.75(11) |
| C2 | 1.1449(12) | 0.2475(10) | 0.3169(4) | 1.80(10) |
| C3 | 1.012(2) | 0.3159(10) | 0.3983(4) | 1.94(10) |
| C4 | 0.8503(12) | 0.4786(9) | 0.3690(4) | 1.52(11) |
| C5 | 0.659(2) | 0.5802(9) | 0.4157(4) | 1.80(11) |
| C6 | 0.5365(12) | 0.7227(10) | 0.3758(4) | 1.63(11) |
| C7 | 0.6039(13) | 0.7793(9) | 0.2942(4) | 1.97(12) |
| C8 | 0.7994(12) | 0.6798(9) | 0.2484(4) | 1.65(11) |
| C9 | 0.916(2) | 0.5260(9) | 0.2861(4) | 1.73(11) |
| C10 | 0.8837(13) | 0.7403(11) | 0.1616(4) | 2.09(11) |
| H1 | 1.3090 | 0.4527 | 0.2402 | 2.10 |
| H2A | 0.8836 | 0.2258 | 0.4229 | 2.32 |
| H3B | 1.1601 | 0.3476 | 0.4414 | 2.32 |
| H4 | 0.6160 | 0.5510 | 0.4731 | 2.16 |
| H5 | 0.5189 | 0.8832 | 0.2702 | 2.36 |
| H6B | 1.0913 | 0.7399 | 0.1579 | 2.51 |
| H7C | 0.8122 | 0.8614 | 0.1515 | 2.51 |
| H8A | 0.8030 | 0.6593 | 0.1185 | 2.51 |
| H9 | 0.8355 | 0.3277 | 0.1523 | 2.15 |
| H10 | 1.53(2) | 0.404(12) | 0.022(6) | 4(2) |
| H11 | 1.23(3) | 0.49(2) | 0.008(8) | 7(3) |

Reference Example 4

X-ray crystallographic analysis of N-[(1S)-4,7-difluoro-2,3-dihydro-1H-inden-1-yl]sulfamide The white solids obtained in Example 19-(2) were dissolved in ethanol recrystallized by solvent evaporation method.

X-ray diffraction analysis was conducted using the obtained single crystal. The results of data collection and crystallographic analysis are summarized in Table 7, and the atomic coordinates are shown in Tables 8. The absolute configuration of the title compound was specified from such results.

TABLE 7

| | |
|---|---|
| Temperature | 300 K |
| Wavelength | 1.5418 Å |
| Crystal system, space group | Monoclinic, P2$_1$ |

TABLE 7-continued

| | |
|---|---|
| Lattice parameters | a = 5.0695(2) Å |
| | b = 6.7428(3) Å |
| | c = 15.4808(6) Å |
| | β = 94.627(2)° |
| Volume | 527.45(4) Å$^3$ |
| Z value, calculated density | 2, 1.557 g/cm$^3$ |
| Crystal dimentions | 0.30 × 0.10 × 0.10 mm |
| Total number of reflections/ number of unique reflections | 3813/1751 [R$_{int}$ = 0.1215] |
| Completeness | 96.7% |
| Structure solution | Direct methods (SIR92) |
| Refinement | Full-matrix least-squares on F$^2$ |
| Reflection/parameter | 1751/145 |
| Goodness of fit indicator | 0.888 |
| R factor (all data) | 0.1244 |
| R factor (I > 2σ (I)) | 0.0781 |
| Flack parameter | 0.00(6) |
| The maximum and minimum peaks on the final difference Fourier map | 0.35 and −0.50 e/Å$^3$ |

TABLE 8

| Atom | x | y | z | B (eq) |
|---|---|---|---|---|
| S1 | 0.2094(4) | −0.2021(4) | 0.4051(2) | 5.37(6) |
| F7 | 0.334(2) | −0.277(1) | 0.1446(5) | 10.6(2) |
| F17 | 0.963(2) | 0.356(2) | 0.1157(5) | 13.3(3) |
| O2 | 0.348(2) | −0.360(1) | 0.4543(4) | 6.9(2) |
| O5 | −0.046(1) | −0.253(1) | 0.3600(4) | 6.4(2) |
| N4 | 0.145(2) | −0.012(2) | 0.4661(5) | 6.5(2) |
| N6 | 0.406(2) | −0.123(2) | 0.3401(4) | 5.7(2) |
| C8 | 0.651(2) | 0.189(2) | 0.1922(6) | 6.5(3) |
| C9 | 0.337(2) | 0.040(2) | 0.2791(6) | 6.1(2) |
| C10 | 0.489(2) | 0.026(2) | 0.1994(6) | 5.8(2) |
| C11 | 0.805(2) | 0.198(2) | 0.1230(7) | 7.5(3) |
| C12 | 0.495(3) | −0.122(2) | 0.1378(7) | 6.9(3) |
| C13 | 0.804(3) | 0.054(3) | 0.0622(7) | 8.4(3) |
| C14 | 0.414(3) | 0.254(2) | 0.3148(7) | 9.8(4) |
| C15 | 0.645(3) | −0.111(2) | 0.0695(7) | 7.5(3) |
| C16 | 0.624(3) | 0.331(2) | 0.2651(8) | 9.8(4) |
| H6 | 0.5601 | −0.1764 | 0.3401 | 6.86 |
| H9 | 0.1472 | 0.0357 | 0.2618 | 7.32 |
| H13 | 0.9096 | 0.0657 | 0.0159 | 10.08 |
| H14A | 0.2609 | 0.3403 | 0.3086 | 11.74 |
| H14B | 0.4746 | 0.2462 | 0.3758 | 11.74 |
| H15 | 0.6406 | −0.2121 | 0.0285 | 8.96 |
| H16A | 0.7888 | 0.3398 | 0.3013 | 11.79 |
| H16B | 0.5781 | 0.4619 | 0.2428 | 11.79 |

Pharmacological Test Examples

The present inventors conducted the following tests for confirming pharmacological activity of the compounds.

These tests are used for evaluating inhibitory effect of a compound against convulsive seizure.

Kindling model is closely reflected epilepsy model to human pathology and shows the good predictivity in human clinical efficacy. Moreover, the level of neurotoxic effects was assessed by measuring the motor impairment/coordination in rota rod test.

The following compound was described in the Patent Literature 1 (Example 4), the Patent Literature 2 (Example 5b) and Non-Patent Literature 2 (Compound 17).

The present inventors prepared it according to the preparation procedure in Patent Literature 1 and used it as a reference compound.

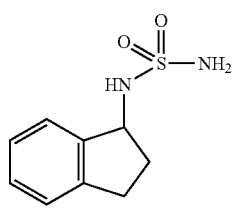 [SMILES: NS(=O)(=O)NC1CCc2ccccc21]

Test Example 1

Mouse Corneal Kindling Model

Male C57Bl/6 mice were stimulated twice daily for 10 days. The electric-stimulations with current intensities of 4.0 mA and duration of 3 s (pulse frequency 50 Hz) were applied via corneally placed saline-soaked copper electrodes.

Seizure severity was ranked according to a modified scoring system of the Racine's scale (Clin. Neurophysiol. 1972: 32:281-294): Score 1, mild facial clonus and eye blinking; 2, severe facial clonus, head nodding, chewing; 3, unilateral or alternating forelimb clonus; 4, bilateral forelimb clonus with rearing; 5, bilateral forelimb clonus with rearing and falling; 6, tonic fore- and/or hindlimb extension. The fully kindled animals with the severity score 4 or more were used for evaluation.

Test compounds were dissolved in the vehicle (0.45% methyl cellulose/4.5% cremophor/10% DMSO), then orally (p.o.) or intraperitoneally (i.p.) administered to mice. The vehicle was orally administered as controls.

Electric stimulation was applied at 1 hour after p.o. or 20 minutes after i.p administration. Stimulation parameters were the same as during the kindling process. After electric stimulation, seizure severity was recorded for 30 seconds according to the Racine's scale.

Four to ten animals were used for calculation of average seizure severity score at each dose. For an effective compound, a reduction in seizure severity score 2 or less was judged to be effective, and effective dosage ($ED_{50}$) where the 50% of animals used in the test showed effectiveness was calculated.

The results of anti-seizure efficacy were shown in table 9. Test compound showed stronger anti-seizure efficacy than the reference compound.

TABLE 9

| Compound No. | Seizure severity score (Average) | | | (route) |
| --- | --- | --- | --- | --- |
| | dose 10 mg/kg | dose 25 mg/kg | dose 50 mg/kg | |
| Reference compound | 4.67 | 3.17 | 1.33 | p.o. |
| 1 | 2 | 0 | 0 | p.o. |
| 2 | 4 | 0 | 0 | p.o. |
| 3 | 1.5 | 0 | ND | p.o. |
| 4 | ND | 0 | 0 | p.o. |
| 5 | 2 | 0 | ND | p.o. |
| 6 | 1 | 0 | 0.25 | p.o. |
| 7 | 3.5 | 0.25 | ND | i.p |
| 8 | 3 | 0 | ND | i.p |
| 9 | ND | 0 | 0 | p.o. |
| 10 | 0 | 0 | ND | p.o. |
| 11 | 0.5 | 0 | ND | p.o. |
| 12 | 0 | 0 | ND | p.o. |
| 13 | 0 | ND | ND | p.o. |
| 14 | ND | 0 | ND | p.o. |

TABLE 9-continued

| Compound No. | Seizure severity score (Average) | | | (route) |
| --- | --- | --- | --- | --- |
| | dose 10 mg/kg | dose 25 mg/kg | dose 50 mg/kg | |
| 15 | 3 | 0 | ND | p.o. |
| 16a | ND | 0 | ND | p.o. |
| 16b | 3.75 | 0.5 | ND | p.o. |
| 17 | 2 | 0 | 0 | p.o. |
| 18 | 2 | 0 | ND | p.o. |
| 19 | 2 | 0 | ND | p.o. |
| 20 | 3.25 | 0 | ND | i.p |
| 21 | 4.25 | 2 | ND | i.p |
| 22a | 3 | 0.25 | ND | p.o. |
| 22b | 3 | 0 | ND | p.o. |
| 23 | 4.25 | 0 | ND | p.o. |
| 24 | 3 | 0 | ND | p.o. |
| 25a | 1.75 | 0 | ND | p.o. |
| 25b | 1 | 0 | ND | p.o. |
| 26 | 4.25 | 0 | ND | p.o. |
| 27 | 3 | 0 | ND | p.o. |
| 28a | 4 | 0 | ND | p.o. |
| 28b | 3.75 | 0 | ND | p.o. |
| 29 | 3.5 | 0.83 | 0 | p.o. |
| 30 | 4.25 | 0.25 | ND | p.o. |
| 31 | 1.5 | 0 | ND | p.o. |

ND: Not done

Test Example 2

Rat Amygdala Kindling Model

Male Wistar Kyoto rats (Charles River Japan) were used for the experiment. For implantation of kindling electrodes, rats were anesthetized with pentobarbital (65 mg/kg i.p.) and a tripolar electrode was implanted into the right hemisphere aimed at the basolateral amygdala using the coordinates derived from the atlas of Paxinos and Watson. Electrical stimulation of the amygdala was initiated following a recovery period of one week after surgery. From the next day on, constant current stimulations (500 µA, 1 ms, monophasic square-wave pulses, 50/s for 1 s) were delivered to the amygdala at intervals of 1 day until at least 3 consecutive fully kindled seizures (stage 5; seizure severity classified according to Racine) were elicited.

The threshold for induction of amygdala after discharges (ADT), i.e., epileptiform spikes on electroencephalogram (EEG), was measured for anti-seizure potency of compounds. In fully kindled rats, the ADT was determined by administering a series of stimulations beginning at 40 to and increasing in steps of about 25% of the previous current. The threshold was defined as the lowest intensity producing after discharges (ADs) with a duration of at least 3 s in the morning of experimental day.

In the afternoon, test compounds were dissolved in the vehicle (a 1:1:1 mixture of polyethylene glycol 200, distilled water and DMSO), then orally administered to rats. The vehicle was orally administered as controls. The ADT was determined again 60 minutes after administration of drugs. The % of pre-value (morning results) was determined for each rat. Results were expressed as mean±SEM and analyzed by Dunnett's multiple comparisons test. (4-9 rats)

Figure 2:
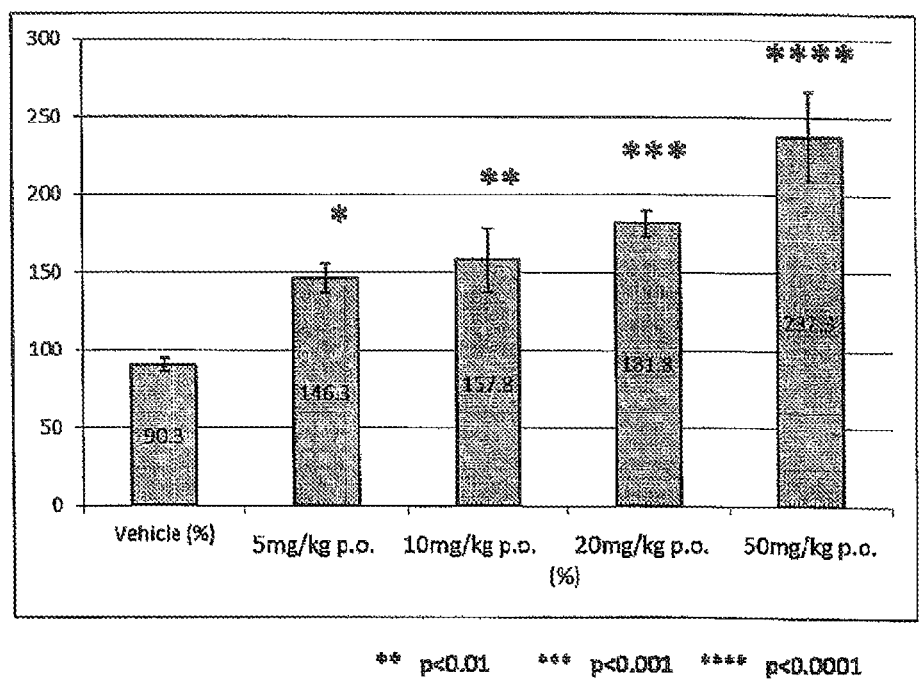
FIG. 2 is a graph showing a result of Test Example 2 by administrating Compound of Example 11.
Figure 3:
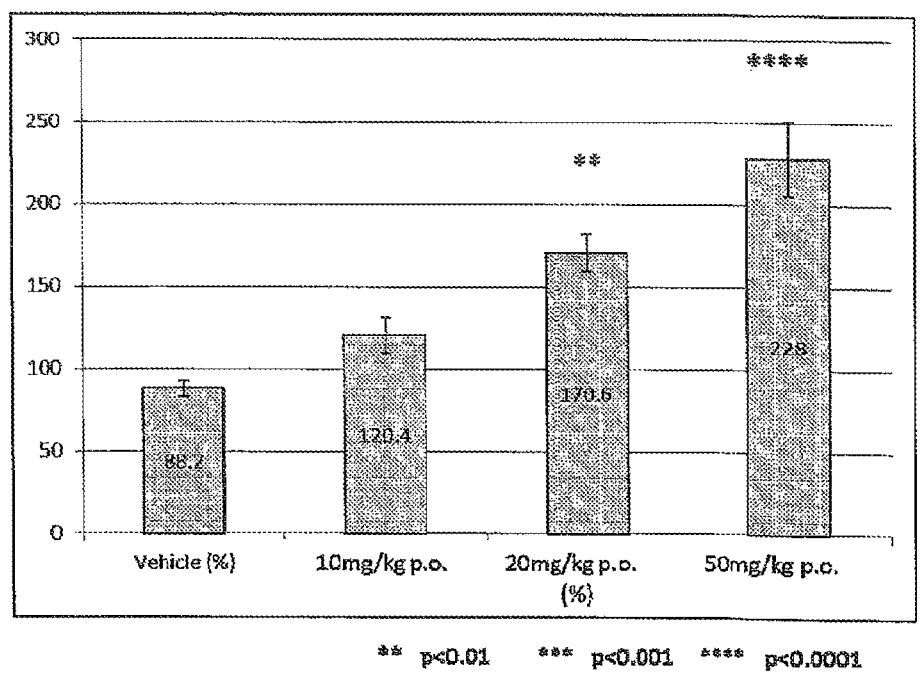
FIG. 3 is a graph showing a result of Test Example 2 by administrating Compound of Example 6.

As shown in FIGS. 1 to 3, the compound of Example 1, 11 and 6 showed dose-dependent elevation of after-discharge threshold in rat amygdala kindling model.

These results indicated suppressive effect of compounds against seizures.

Test Example 3

Rota Rod Test

Rotarod apparatus (Rota-rod MK-660C, Muromachi-Kikai Co., Ltd.) was used for measurement. The motor was turned on and the rod rotation was continuously accelerated to a rate of 40 rpm over 180 sec.

Male ddY mice at an age of 5 weeks (Japan SLC) were used. On the experiment day, the mice were pretrained and only the animals able to remain on the rod for at least 60 s were selected for experiment.

Test compounds were dissolved in the vehicle (0.45% methyl cellulose/4.5% cremophor/10% dimethyl sulfoxide), then orally (p.o.) administered to mice. The vehicle was orally administered as controls. The effects of compounds were studied in groups of six to ten animals.

Latency for mice to fall off from the rod was measured. The toxic dose at which fall off latency shorten by 50% of vehicle control value ($TD_{50}$) was calculated.

Therapeutic index were calculated by dividing the respective $TD_{50}$ value in rota rod test by the $ED_{50}$ value determined in the corneal kindling model.

The calculated $ED_{50}$, $TD_{50}$ and therapeutic index of each compound were shown in Table 10. Thus, the compounds evaluated in this Test Example 3 were identified with high therapeutic index value indicating safer compounds than the reference compound.

TABLE 10

| Compound (Example No.) | $ED_{50}$ | $TD_{50}$ | Therapeutic index | route |
|---|---|---|---|---|
| Control | 40 | 211 | 5.27 | p.o. |
| 1 | 7.9 | 390 | 49.4 | p.o. |
| 2 | 15.4 | >200 | >13.0 | p.o. |
| 5 | 5.7 | 404 | 70.9 | p.o. |
| 6 | 10.2 | 307 | 30.1 | p.o. |
| 8 | 10.6 | 119 | 11.2 | i.p |
| 11 | 5 | 132 | 26.4 | p.o. |
| 12 | 5.6 | 143 | 25.5 | p.o. |
| 19 | 12.4 | 235 | 19.0 | p.o. |
| 21 | 10.6 | 234 | 22.1 | p.o. |
| 29 | 15.8 | 157 | 9.93 | p.o. |

The invention claimed is:

1. A compound selected from the group consisting of:
   1) N-[(1S)-2,2,5,7-tetrafluoro-2,3-dihydro-1H-inden-1-yl]sulfamide,
   2) N-[(1S)-2,2,4,7-tetrafluoro-2,3-dihydro-1H-inden-1-yl]sulfamide,
   3) (+)-N-(2,2,4,6,7-pentafluoro-2,3-dihydro-1H-inden-1-yl)sulfamide,
   4) N-[(1S*)-5-cyano-2,2-difluoro-7-methyl-2,3-dihydro-1H-inden-1-yl]sulfamide,
   5) (−)-N-(7-chloro-2,2,5-trifluoro-2,3-dihydro-1H-inden-1-yl)sulfamide,
   6) (−)-N-(7-chloro-2,2,4-trifluoro-2,3-dihydro-1H-inden-1-yl)sulfamide,
   7) (−)-N-(7-chloro-2,2-difluoro-2,3-dihydro-1H-inden-1-yl)sulfamide,
   8) (−)-N-(7-chloro-2,2,6-trifluoro-2,3-dihydro-1H-inden-1-yl)sulfamide,
   9) (+)-N-(5-chloro-2,2,7-trifluoro-2,3-dihydro-1H-inden-1-yl)sulfamide,
   10) N-[(1S)-2,2-difluoro-7-methyl-2,3-dihydro-1H-inden-1-yl]sulfamide,
   11) N-[(1S)-2,2,5-trifluoro-7-methyl-2,3-dihydro-1H-inden-1-yl]sulfamide,
   12) N-[(1S*)-2,2,4-trifluoro-7-methyl-2,3-dihydro-1H-inden-1-yl]sulfamide,
   13) N-[(1S*)-7-(difluoromethyl)-2,2-difluoro-2,3-dihydro-1H-inden-1-yl]sulfamide,
   14) N-[(1R*,2R*)-2,4,7-trifluoro-2,3-dihydro-1H-inden-1-yl]sulfamide,
   15) (−)-N-[(1R*,2R*)-7-chloro-2,4-difluoro-2,3-dihydro-1H-inden-1-yl]sulfamide,
   16) (+)-N-[(1R*,2R*)-7-chloro-2,4-difluoro-2,3-dihydro-1H-inden-1-yl]sulfamide,
   17) (−)-N-[(1R*,2R*)-7-chloro-2,5-difluoro-2,3-dihydro-1H-inden-1-yl]sulfamide,
   18) (+)-N-[(1R*,2R*)-4-chloro-7-fluoro-2-methoxy-2,3-dihydro-1H-inden-1-yl]sulfamide,
   19) (+)-N-(7-chloro-4-fluoro-2,3-dihydro-1H-inden-1-yl)sulfamide,
   20) (±)-N-(5-fluoro-7-methyl-2,3-dihydro-1H-inden-1-yl)sulfamide,
   21) (−)-N-(4-fluoro-7-methyl-2,3-dihydro-1H-inden-1-yl)sulfamide,
   22) (+)-N-(4-fluoro-7-methyl-2,3-dihydro-1H-inden-1-yl)sulfamide,
   23) (+)-N-(7-methyl-2,3-dihydro-1H-inden-1-yl)sulfamide,
   24) (±)-N-(5-chloro-7-methyl-2,3-dihydro-1H-inden-1-yl)sulfamide,
   25) (−)-N-(4-chloro-7-fluoro-2,3-dihydro-1H-inden-1-yl)sulfamide,
   26) (+)-N-(7-chloro-5-cyano-2,3-dihydro-1H-inden-1-yl)sulfamide,
   27) (−)-N-(7-chloro-5-cyano-2,3-dihydro-1H-inden-1-yl)sulfamide,
   28) (−)-N-(5-chloro-7-fluoro-2,3-dihydro-1H-inden-1-yl)sulfamide,
   29) N-[(1S)-4,7-difluoro-2,3-dihydro-1H-inden-1-yl]sulfamide,
   30) (+)-N-(7-chloro-2,3-dihydro-1H-inden-1-yl)sulfamide,
   31) (+)-N-(5-cyano-7-methyl-2,3-dihydro-1H-inden-1-yl)sulfamide,
   32) (−)-N-(5-cyano-7-methyl-2,3-dihydro-1H-inden-1-yl)sulfamide,
   33) N-[(1S)-7-chloro-5-fluoro-2,3-dihydro-1H-inden-1-yl]sulfamide, and
   34) (−)-N-(4,6,7-trifluoro-2,3-dihydro-1H-inden-1-yl)sulfamide,
   or a pharmaceutically acceptable salt thereof.

2. A compound selected from the group consisting of:
   1) N-[(1S)-2,2,5,7-tetrafluoro-2,3-dihydro-1H-inden-1-yl]sulfamide,
   2) N-[(1S)-2,2,4,7-tetrafluoro-2,3-dihydro-1H-inden-1-yl]sulfamide,
   3) (−)-N-(7-chloro-2,2,5-trifluoro-2,3-dihydro-1H-inden-1-yl)sulfamide,
   4) (−)-N-(7-chloro-2,2-difluoro-2,3-dihydro-1H-inden-1-yl)sulfamide,
   5) N-[(1S)-2,2-difluoro-7-methyl-2,3-dihydro-1H-inden-1-yl]sulfamide,
   6) N-[(1S)-2,2,5-trifluoro-7-methyl-2,3-dihydro-1H-inden-1-yl]sulfamide,
   7) N-[(1S)-4,7-difluoro-2,3-dihydro-1H-inden-1-yl]sulfamide,
   8) N-[(1S)-7-chloro-5-fluoro-2,3-dihydro-1H-inden-1-yl]sulfamide, and 9) (−)-N-(4,6,7-trifluoro-2,3-dihydro-1H-inden-1-yl)sulfamide, or a pharmaceutically acceptable salt thereof.

3. N-[(1S)-2,2,5-trifluoro-7-methyl-2,3-dihydro-1H-inden-1-yl]sulfamide or a pharmaceutically acceptable salt thereof.

4. (−)-N-(7-chloro-2,2,5-trifluoro-2,3-dihydro-1H-inden-1-yl)sulfamide or a pharmaceutically acceptable salt thereof.

5. N-[(1S)-2,2,5,7-tetrafluoro-2,3-dihydro-1H-inden-1-yl]sulfamide or a pharmaceutically acceptable salt thereof.

6. The compound or the pharmaceutically acceptable salt thereof according to claim 1, wherein the compound is N-[(1S)-2,2-difluoro-7-methyl-2,3-dihydro-1H-inden-1-yl]sulfamide.

7. The compound or the pharmaceutically acceptable salt thereof according to claim 1, wherein the compound is N-[(1S)-4,7-difluoro-2,3-dihydro-1H-inden-1-yl]sulfamide.

8. A pharmaceutical composition comprising the compound or pharmaceutically acceptable salt thereof according to claim 1.

9. A method for treating epilepsy in a subject in need thereof comprising administering to the subject a pharmacologically effective dose of the compound or the pharmaceutically acceptable salt thereof according to claim 1.

10. A pharmaceutical composition comprising the compound or pharmaceutically acceptable salt thereof according to claim 3.

11. A method for treating epilepsy in a subject in need thereof comprising administering to the subject a pharmacologically effective dose of the compound or the pharmaceutically acceptable salt thereof according to claim 3.

12. A pharmaceutical composition comprising the compound or pharmaceutically acceptable salt thereof according to claim 4.

13. A method for treating epilepsy in a subject in need thereof comprising administering to the subject a pharmacologically effective dose of the compound or the pharmaceutically acceptable salt thereof according to claim 4.

14. A pharmaceutical composition comprising the compound or pharmaceutically acceptable salt thereof according to claim 5.

15. A method for treating epilepsy in a subject in need thereof comprising administering to the subject a pharmacologically effective dose of the compound or the pharmaceutically acceptable salt thereof according to claim 5.

16. A pharmaceutical composition comprising the compound or pharmaceutically acceptable salt thereof according to claim 6.

17. A method for treating epilepsy in a subject in need thereof comprising administering to the subject a pharmacologically effective dose of the compound or the pharmaceutically acceptable salt thereof according to claim 6.

18. A pharmaceutical composition comprising the compound or pharmaceutically acceptable salt thereof according to claim 7.

19. A method for treating epilepsy in a subject in need thereof comprising administering to the subject a pharmacologically effective dose of the compound or the pharmaceutically acceptable salt thereof according to claim 7.

* * * * *